US006420586B1

(12) United States Patent
Hanson et al.

(10) Patent No.: US 6,420,586 B1
(45) Date of Patent: Jul. 16, 2002

(54) AMINO ACID-DERIVED CYCLIC PHOSPHONAMIDES AND METHODS OF SYNTHESIZING THE SAME

(75) Inventors: Paul R. Hanson; Kevin T. Sprott; Matthew D. McReynolds, all of Lawrence, KS (US)

(73) Assignee: University of Kansas, Lawrence, KS (US)

( * ) Notice: Subject to any disclaimer, the term of this patent is extended or adjusted under 35 U.S.C. 154(b) by 52 days.

(21) Appl. No.: 09/639,051

(22) Filed: Aug. 15, 2000

(51) Int. Cl.$^7$ ................................................ C07F 9/645
(52) U.S. Cl. .......................................................... 558/81
(58) Field of Search ............................................ 558/81

(56) References Cited

U.S. PATENT DOCUMENTS

| 3,329,687 A | 7/1967 | Houlihan |
| 5,312,940 A | 5/1994 | Grubbs et al. |
| 5,342,909 A | 8/1994 | Grubbs et al. |
| 5,506,355 A | 4/1996 | Jadhav et al. |
| 5,610,294 A | 3/1997 | Lam et al. |
| 5,710,298 A | 1/1998 | Grubbs et al. |
| 5,750,815 A | 5/1998 | Grubbs et al. |
| 5,917,071 A | 6/1999 | Grubbs et al. |
| 6,048,993 A | 4/2000 | Grubbs et al. |

FOREIGN PATENT DOCUMENTS

| WO | 9419329 | 9/1994 |
| WO | 9937643 | 7/1999 |

OTHER PUBLICATIONS

Zhu, S. et al., "Chiral Mo–Binol Complexes: Activity, Synthesis, and Structure. Efficient Enantioselective Six–Membered Ring Synthesis Through Catalytic Metalhesis" *J. Am. Chem. Soc.,* 1999, 121, 8251–8259.

Kingsbury, J. et al., "A Recyclable Ru–Based Metalhesis Catalyst", *J. Am. Chem. Soc.,* 1999, 121, 791–799.

Scholl, M. et al., Synthesis and Activity of a New Generation of Ruthenium–Based Olefin Metathesis Catalysts Coordinated With 1,3–Dimesityl–4,5–dihydroimidazol–2–ylidene Ligands$^§$, *Org. Lett.,* vol. 1, No. 6, 1999, 953–956.

Totland, K. et al., "Ring Opening Metalthesis Polymerization With Binaphtholate or Biphenolate Complexes of Molybdenum", *Macromolecules,* 1996, 29, 6114–6125.

Alexander, J. et al., "Catalytic Enantioselective Ring–Closing Metathesis by a Chiral Biphen–Mo Complex", *J. Am. Chem. Soc.,* 1998, 120, 4041–4042.

Bäckbro, K., "Unexpected Binding Mode of Cyclic Sulfamide HIV–1 Protease Inhibitor", *J. Med. Chem.,* 1997, 40, 898–902.

Hultén, J. et al., "Inhibitors of the $c_2$–Symmetric HIV–1 Protease: Nonsymmetric Binding of a Symmetric Cyclic Sulfamide With Ketoxime Groups in the P2/P2' Side Chains", *J. Med. Chem.,* 1999, 42, 4054–4061.

*Primary Examiner*—T. A. Solola
(74) *Attorney, Agent, or Firm*—Hovey Williams LLP

(57) ABSTRACT

New phosphonamide compounds and methods of forming those compounds are provided. In one embodiment, the inventive methods comprise subjecting an opened-ring phosphonamide template to a ring-closing metathesis reaction in the presence of a ring-closing catalyst (e.g., a Grubbs catalyst) to yield a phosphonamide. In another embodiment, the inventive methods comprise reacting a template structure with a phosphorus (III) compound to yield the phosphonamide. Advantageously, in either embodiment, the template structures can be provided with a wide array of functional groups (e.g., amino acid side chains, peptides) chosen to provide particular properties to the compound.

3 Claims, No Drawings

AMINO ACID-DERIVED CYCLIC PHOSPHONAMIDES AND METHODS OF SYNTHESIZING THE SAME

BACKGROUND OF THE INVENTION

1. Field of the Invention

The present invention is directed towards new phosphonamide compounds and methods of forming those compounds via ring-closing metathesis reactions carried out in the presence of a ring-closing catalyst (e.g., a Grubbs catalyst), or via reacting a template structure with a phosphorus (III) compound to yield complex phosphonamides. The compounds have a number of uses including as inhibitors of enzymes such as HIV proteases.

2. Description of the Prior Art

Small peptides are excellent starting points for drug design because they have the potential to overcome the pharmnacokinetic shortcomings of larger peptides, yet retain the desirable quality of molecular recognition. A number of dipeptides are currently being developed as novel pharmaceutical agents (see e.g., Blackburn et al., *Bioorg. Med. Chem. Lett.*, 7:823–26 (1997); Schullek et al., *Anal. Biochem.*, 246:20–29 (1997), each incorporated by reference herein). Unfortunately, even small peptides suffer from proteolytic instability which limits their use as drug candidates.

Peptide mimics have been developed which utilize the urea moiety as a non-hydrolyzable linker and/or a hydrogen bond acceptor. Further modifications to cyclic ureas have led to the generation of a new sub-class of biologically active compounds. A number of cyclic HIV protease inhibitors have been developed that incorporate ureas, sulfamides, and other urea surrogates as the central linchpin. In these cases, it has been shown that the H-bonding urea moieties may serve to replace the water molecule exclusive to the active site of HIV protease. Ring-closing metathesis (RCM) reactions have become a highly effective strategy for the construction of a number of important heterocyclic compounds (see e.g., Fu et al., *J. Am. Chem. Soc.*, 115:9856 (1993), incorporated by reference herein) and constrained peptides (see e.g., Miller et al., *J. Am. Chem. Soc.*, 117:5855–5856 (1995); Miller et al., *J. Am. Chem. Soc.*, 118:9606–9614 (1996); Blackwell et al., *Angew. Chem., Int. Ed.*, 37:3281–3284 (1998), each incorporated by reference herein).

Since its discovery as the causative agent of AIDS, considerable effort has been placed on understanding the biomolecular replicative process of the human immunodeficiency virus (HIV), with primary focus being placed on the inhibition of a key virally encoded protease enzyme of the pol gene. Many synthetic approaches to the inhibition of HIV protease are based on the synthesis of peptidomimetics which replace a key scissile amide bond by a non-hydrolyzable transition state isostere. This strategy has been employed to synthesize a number of novel nonpeptidal HIV protease inhibitors. Among the more effective peptidomimetics, the synthesis of cyclic ureas (see e.g., Lucca et al., *Drugs of the Future*, 23:987 (1998)), cyclic sulfamides (see e.g., Jadhav et al., *Tetrahedron Lett.*, 36:6383 (1995)), hydroxyethylene/hydroxyethylamine isosteres (see e.g., Thomas et al., *Biorg. Med. Chem. Lett.*, 4:2759 (1994)) have been reported.

Finally, phosphorus-containing compounds have gained considerable attention due to their diverse biological and chemical profiles. A number of P-heterocycles have shown potent biological activity and have thus become attractive targets as rationally designed small molecules (see e.g., Zon, *Progr. Med. Che.*, 19:205–46 (1982); Nachev, *Bull. Chem. Soc. Jpn.*, 61:3705–9 (1988); and Stec, *J. Organophosphorus Chem.*, 13:145–74 (1982), each incorporated by reference herein).

SUMMARY OF THE INVENTION

The present invention is broadly concerned with new phosphonamide compounds and methods of forming such compounds.

In more detail, the preferred compounds are represented by a formula selected from the group consisting of

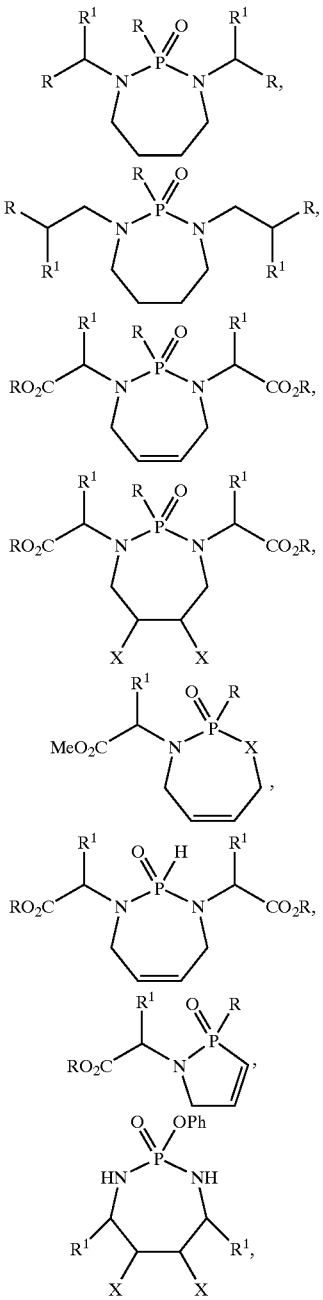

-continued

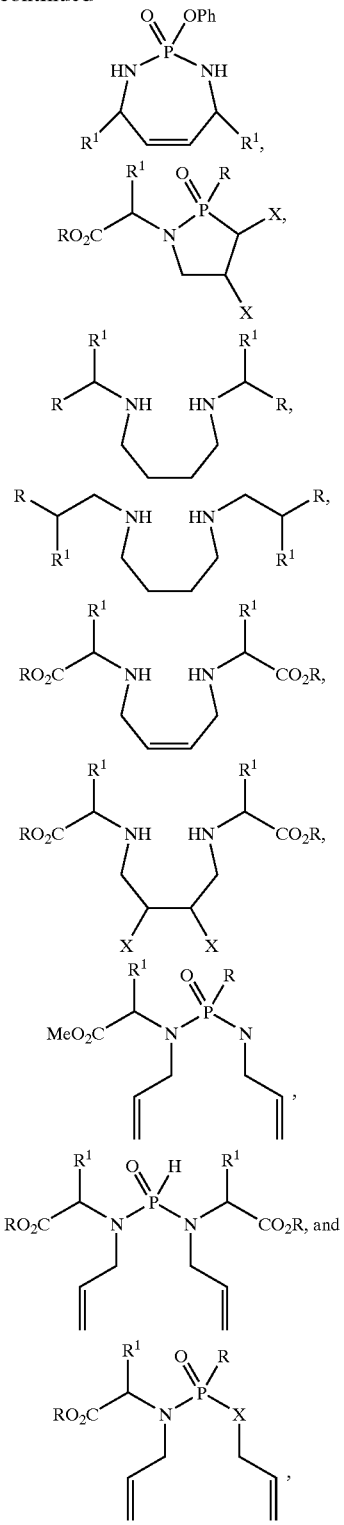

wherein:
- each X is individually selected from the group consisting of oxygen, —NH, and —NOR;
- each R is individually selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, acyl groups (preferably $C_1$–$C_{18}$, more preferably $C_1$–$C_8$), aryl groups (preferably $C_6$–$C_{12}$), 2–15 mer peptides, and benzyl groups; and
- each $R^1$ is individually selected from the group consisting of hydrogen, amino acid side chains, and 2–15 mer peptides.

Preferably at least one $R^1$ group comprises an amino acid side chain selected from the group consisting of

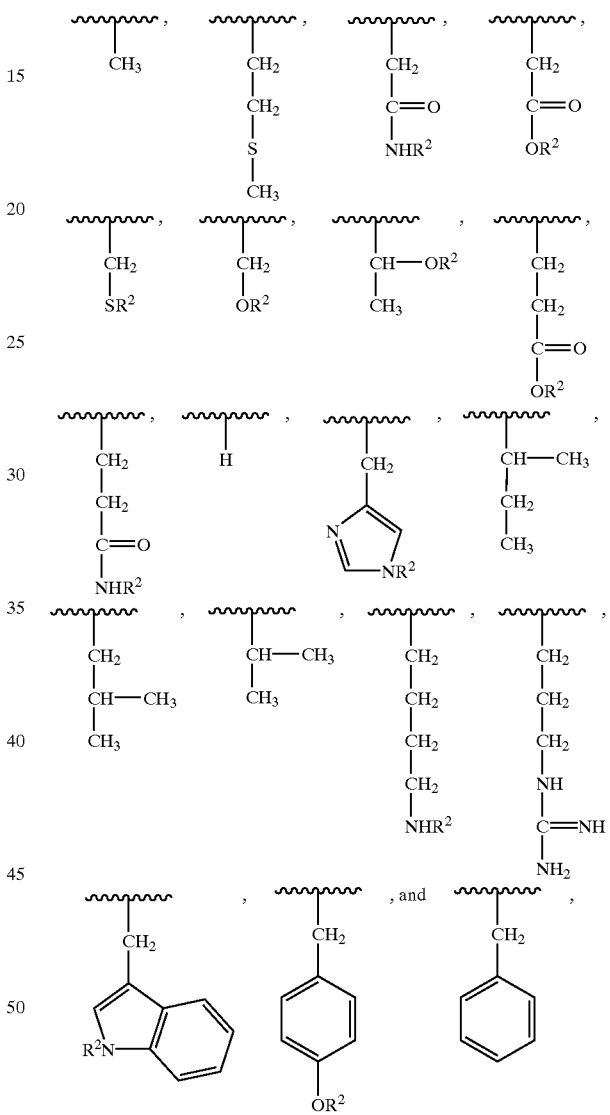

wherein each $R^2$ is individually selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, aryl groups (preferably $C_6$–$C_{12}$), acyl groups (preferably $C_1$–$C_{18}$, more preferably $C_1$–$C_8$), and benzyl groups.

In a preferred embodiment, the inventive compounds comprise a formula selected from the group consisting of

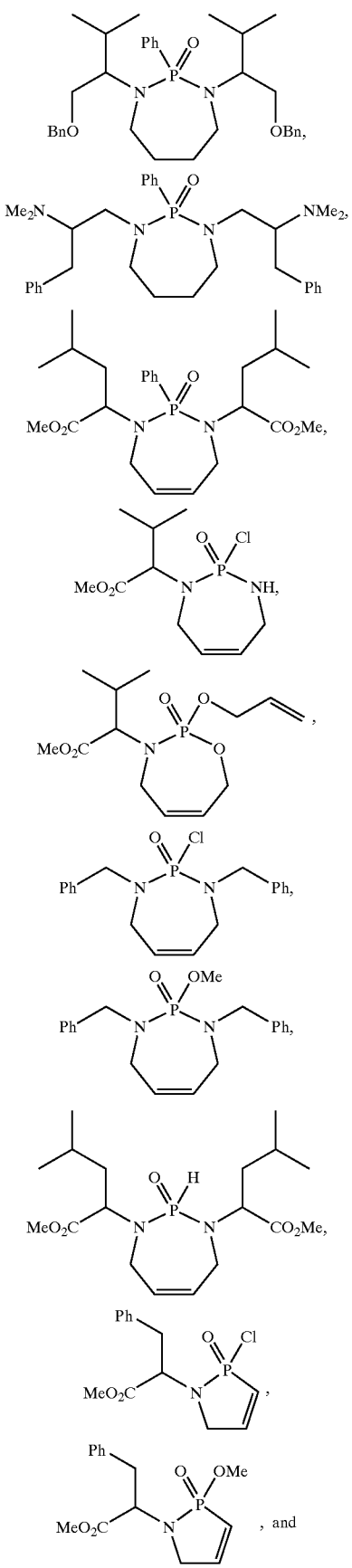

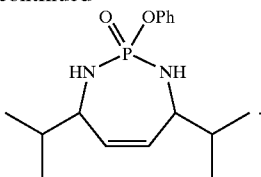

Some of the inventive compounds are formed by reacting a template phosphonamide compound which comprises an opened-ring structure (i.e., a partially-formed ring comprising at least half, but not all of the sides necessary to form a cyclic compound) with a ring-closing catalyst to yield the closed-ring phosphonamide compound. Preferred ring-closing catalysts are Grubbs catalysts (see e.g., U.S. Pat. Nos. 6,048,993, 5,917,071, 5,750,815, 5,710,298, 5,342,909, and 5,312,940, each incorporated by reference herein) as well as those disclosed by the following references, each also incorporated by reference herein: Matthias, *Org. Ltrs.*, 1(6):953–56 (1999); Schrock, *Macromolecules*, 29(19):6114–25 (1996); Zhu et al., *J. Amer. Chem. Soc.*, 121(36):8251–59 (1999); Alexander et al., *J. Amer. Chem. Soc.*, 120(16):4041–42 (1998); and Kingsbury et al., *J. Amer. Chem. Soc.*, 121(4):791–99 (1999).

Particularly preferred Grubbs catalysts are those selected from the group consisting of

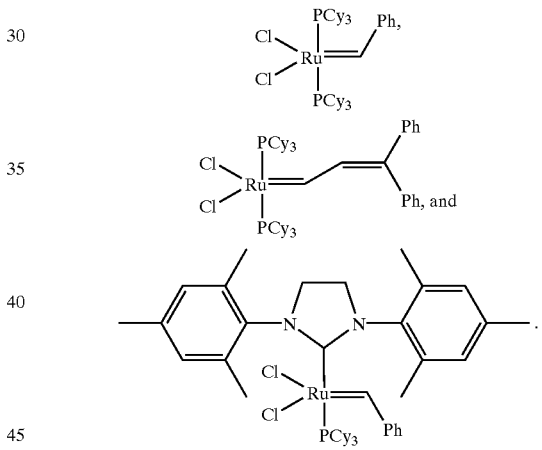

Preferred template opened-ringed structures comprise an allylated phosphonamide, with particularly preferred template structures being those selected from the group consisting of

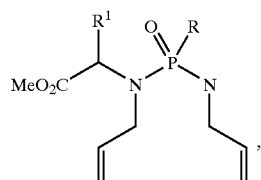

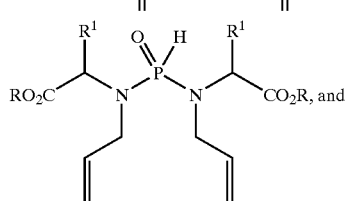

-continued

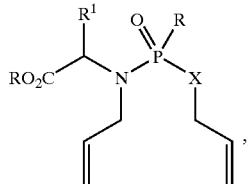

wherein:

each X is individually selected from the group consisting of oxygen, —NH, and —NOR;

each R is individually selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, acyl groups (preferably $C_1$–$C_{18}$, more preferably $C_1$–$C_8$), aryl groups (preferably $C_6$–$C_{12}$), 2–15 mer peptides, and benzyl groups; and each $R^1$ is individually selected from the group consisting of hydrogen, amino acid side chains, and 2–15 mer peptides.

Preferred closed-ring phosphonamide compounds formed by this inventive method are those selected from the group consisting of

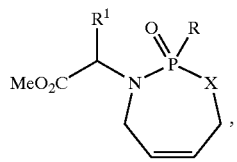

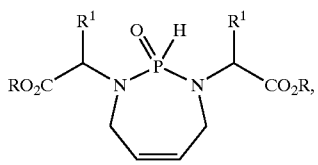

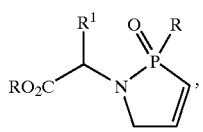

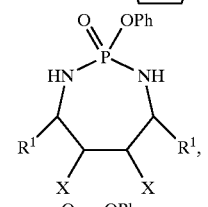

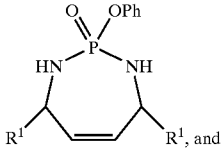

and

-continued

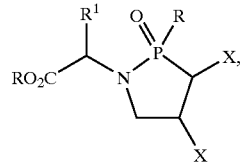

wherein:

each X is individually selected from the group consisting of oxygen, —NH, and —NOR;

each R is individually selected from the group consisting of hydrogen, branched and unbranched alkyl groups (preferably $C_1$–$C_{18}$, more preferably $C_1$–$C_8$),. branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, acyl groups (preferably $C_1$–$C_{18}$, more preferably $C_1$–$C_8$), aryl groups (,preferably $C_6$–$C_{12}$), 2–15 mer peptides, and benzyl groups; and each $R^1$ is individually selected from the group consisting of hydrogen, amino acid side chains, and 2–15 mer peptides.

Preferably the reacting step is carried out at a temperature of from about 15–80° C., and more preferably from about 30–55° C. Furthermore, the reacting step should be carried out in a solvent system comprising a solvent selected from the group consisting of toluene, benzene, chlorobenzene, dichlorobenzene, methylene chloride, dimethoxyethane (DME), and mixtures thereof. Preparing the phosphonamide compounds according to the inventive methods should result in a yield of those compounds of at least about 80%, and preferably at least about 95%, wherein the theoretical yield is taken as 100%.

In another embodiment, the sterically demanding inventive compounds can be prepared with relative ease by providing a template compound comprising two secondary amines bonded to an alkyl chain with the nitrogen atoms of the respective amines being separated by at least two carbon atoms, and preferably at least four carbon atoms, on the alkyl chain. The template compound is then reacted with a phosphorus (III) compound under conditions to cause the phosphorus atom thereof to bond with each of the amine nitrogen atoms, thus forming a cyclic phosphonamide.

Preferred phosphorus (III) compounds have the formula $R^3PY_2$, wherein:

$R^3$ is selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, acyl groups (preferably $C_1$–$C_{18}$, more preferably $C_1$–$C_8$), aryl groups (preferably $C_6$–$C_{12}$), and benzyl groups; and each Y is individually selected from the group consisting of the halogens.

Even more preferably, the phosphorus (III) compound comprises the formula $PhPCl_2$.

Preferred templates have a general formula selected from the group consisting of

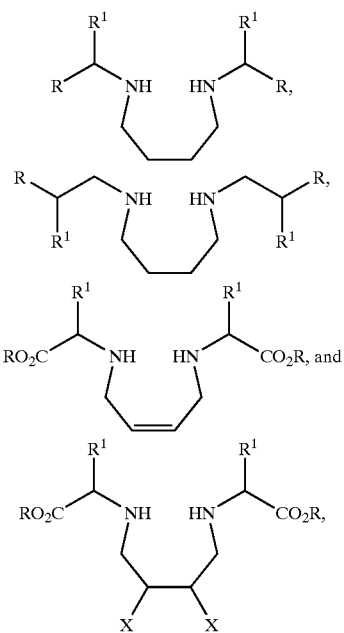

wherein:
  each X is individually selected from the group consisting of oxygen, —NH, and —NOR;
  each R is individually selected from the group consisting of 2–15 mer peptides, hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, acyl groups (preferably $C_1$–$C_{18}$, more preferably $C_1$–$C_8$), aryl groups (preferably $C_6$–$C_{12}$), and benzyl groups; and
  each $R^1$ is individually selected from the group consisting of hydrogen, amino acid side chains, and 2–15 mer peptides.

Preferred cyclic phosphonamides formed according to this method include those selected from the group consisting of

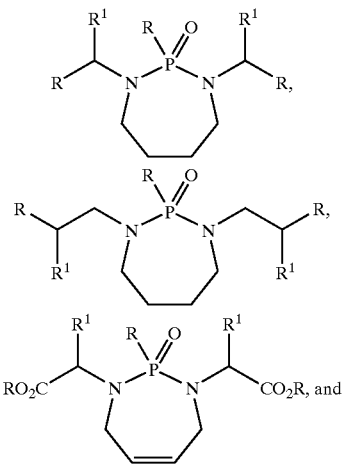

-continued

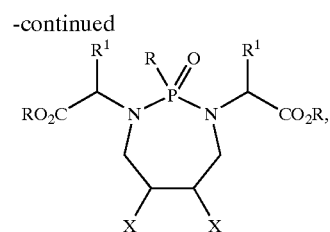

wherein:
  each X is individually selected from the group consisting of oxygen, —NH, and —NOR;
  each R is individually selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, acyl groups (preferably $C_1$–$C_{18}$, more preferably $C_1$–$C_8$), aryl groups (preferably $C_6$–$C_{12}$), 2–15 mer peptides, and benzyl groups; and
  each $R^1$ is individually selected from the group consisting of hydrogen, amino acid side chains, and 2–15 mer peptides.

Preferably the reacting step is carried out at a temperature of from about −10–25° C., and more preferably from about −10–0° C. Furthermore, the reacting step should be carried out in a solvent system comprising a solvent selected from the group consisting of methylene chloride, acetonitrile, diethyl ether, and mixtures thereof. Preparing the phosphonamide compounds according to this embodiment of the inventive methods should result in a yield of those compounds of at least about 80%, and preferably at least about 95%, wherein the theoretical yield is taken as 100%.

It will be appreciated that the inventive methods allow for the synthesis of a wide array of both symmetric and unsymmetric cyclic phosphonamide compounds. Furthermore, the inventive methods allow for preparation of, or selection of, templates having particular functional groups bonded thereto which are then readily formed into the desired phosphonamide in a controlled and repeatable manner. Because the method can be adapted to form phosphonamide compounds comprising one or more amino acid side chains or peptides bonded thereto, the inventive compounds can be used to inhibit enzymes such as HIV protease.

DETAILED DESCRIPTION OF THE PREFERRED EMBODIMENTS

EXAMPLES

The following examples set forth preferred methods in accordance with the invention. It is to be understood, however, that these examples are provided by way of illustration and nothing therein should be taken as a limitation upon the overall scope of the invention.

A number of abbreviations are used herein. These abbreviations and the term or terms that they represent are set forth in Table A.

TABLE A

| Abbreviation | Term(s) |
|---|---|
| hex | hexane |
| Bn | benzyl |
| Ph | phenyl |
| Me | methyl |
| Et | ethyl |
| EtOAc | ethyl acetate |
| Et$_3$N | triethyl amine |

Grubbs Catalysts were used in some of the following Examples. These catalysts are referred to as follows:

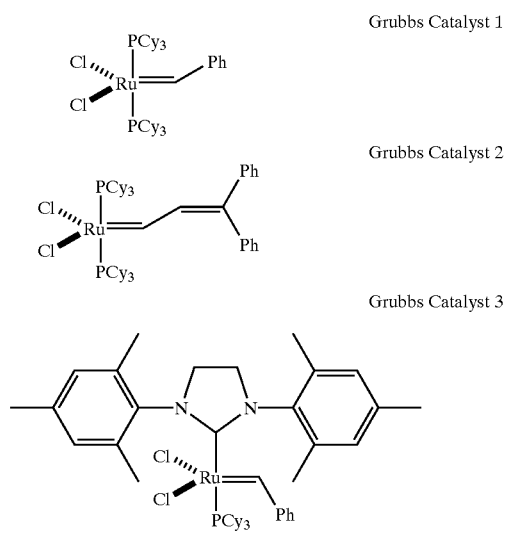

Example 1

Scheme A depicts the general overall reaction scheme followed in Parts I–V below.

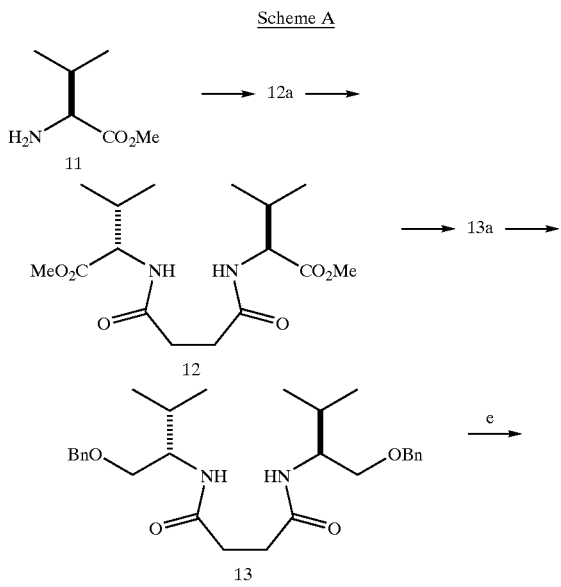

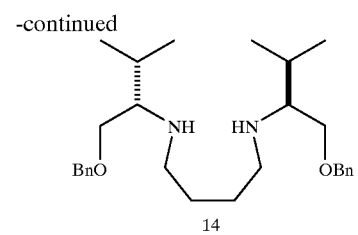

In this and the following procedure descriptions, the number/letter abbreviation depicted in the particular reaction scheme follows the chemical name of the particular compound (e.g., "(11)" follows "valine methyl ester").

I. Preparation of Valine-Derived Diamide (12a)

A solution of valine methyl ester (11) (3.80 g, 28.9 mmol), Et$_3$N (5.24 mL, 37.7 mmol), and dimethyl formamide (DMF) (30 mL) was cooled in a −10° C. (NaCl saturated) ice bath. Fumaryl Chloride (1.42 mL, 13.2 mmol) was added drop-wise over a 1.5 hour period. After addition was complete, the reaction was warmed to room temperature and stirred for 15 minutes. The resulting slurry was portioned between EtOAc (100 mL) and water (100 mL). The water layer was extracted twice with EtOAc (30 mL), and the combined organic layers were dried (Na$_2$SO$_4$) and concentrated under reduced pressure. The resulting white solid was dissolved in minimal, hot CH$_2$Cl$_2$, and crystallized from hexanes to afford 4.43 g (98%) of (12a) as white crystals. $[\alpha]^{25}$=+8.3 (c=0.47, CHCl$_3$); FTIR (neat) 1740, 1637, 1540, 1436, 1355 cm$^{-1}$; $^1$HNMR (400 MHz, CDCl$_3$) δ 7.06 (s, 2H), 7.05 (d, J=10.3 Hz, 2H), 4.69 (dd, J=9.0, 5.3 Hz, 2H), 3.74 (s, 6H), 2.20 (m, 2H), 0.94 (d, J=6.9 Hz, 6H), 0.91 (d, J=6.9 Hz, 6H); $^{13}$C NMR (100 MHz, CDCl$_3$) δ 172.44, 164.24, 133.25, 57.34, 52.26, 31.29, 18.92, 17.84; HRMS calculated for C$_{16}$H$_{27}$N$_2$O$_6$(M+H)$^+$ required 343.1869, found 343.1840.

II. Preparation of Valine-Derived Diamide (12)

Compound (12a) (970 mg, 3.8 mmol) was dissolved in CH$_2$Cl$_2$ (50 mL) in a 100 mL flask under argon atmosphere. Next, 10% palladium on charcoal (Pd/C, 440 mg) was added to the solution and hydrogen gas was purged over the reaction mixture for 5 minutes. The solution was then stirred at room temperature under 1 atm of hydrogen gas for 30 minutes. Filtration of the solution over a pad of Celite followed by concentration thereof yielded 973 mg (99%) of (12) as white crystals. $[\alpha]^{25}$+13.0, (c=0.83; CHCl$_3$); FTIR (neat) 1748, 1641, 1436, 1374 cm$^{-1}$; $^1$H NMR (400 MHz, CDCl$_3$) δ 6.53 (d, J=8.6 Hz, 2H), 4.50 (dd, J=8.7, 5.1 Hz, 2H), 3.70 (s, 6H), 2.67–2.49 (m, 4H), 2.16–2.07 (m, 2H), 0.90 (d, J=6.9 Hz, 6H), 0.87 (d, J=6.9 Hz, 6H); $^{13}$C NMR (100 MHz, CDCl$_3$) δ 172.42, 172.01, 57.16, 52.03, 31.46, 31.05, 18.89, 17.76; HRMS calculated for C$_{16}$H$_{29}$N$_2$O$_6$(M+H)$^+$ required 345.2026, found 34.2042.

III. Preparation of Valine-Derived Diol (13a)

NaBH$_4$ (669 mg, 17.6 mmol) was added at room temperature to a solution of compound (12) (1.21 g, 3.5 mmol) and tetrahydrofuran (THF) (17 ml), and the reaction vessel was equipped with a condenser and heated to 55° C. MeOH was added drop-wise over a 20 minute period, and the reaction was monitored by TLC. The reaction mixture was cooled to room temperature and quenched slowly with a minimal amount of distilled water. The reaction slurry was then subjected to flash chromatography (10% MeOH in EtOAc) to afford 954 mg (95%) of (13a) as white crystals. $[\alpha]^{25}=-18.2$ (c=0.49, 1:1 $CH_3CN:H_2O$); FTIR (neat) 1635, 1543, 1457, 1418 $cm^{-1}$; $^1H$ NMR (400 MHz, $CDCl_3$) δ 6.63 (d, J=8.9 Hz, 2H), 3.99 (s, 2H), 3.76–3.67 (m, 4H), 3.50 (dd, J=10.9, 7.8 Hz, 2H), 2.71 (d, J=9.8 Hz, 2H), 2.49 (d, J=9.9 Hz, 2H), 1.82–1.74 (m, 2H), 0.93 (d,J=6.8 Hz, 6H), 0.91 (d,J=6.8 Hz, 6H); $^{13}C$ NMR(100 MHz, $CDCl_3$) δ 173.63, 63.29, 57.06, 32.27, 29.30, 19.48, 18.79; HRMS calculated for $C_{14}H_{29}N_2O_4$ $(M+H)^+$ required 289.2127, found 289.2152.

IV. Preparation of Valine-Derived Bis-Benzyl Ether (13)

A solution of compound (13a) (20 mg, 0.07 mmol) and DMF (150 μl) was cooled in a 0° C. ice bath. NaH (8.4 mg, 0.22 mmol) was added, and the reaction was warmed to room temperature. After gas evolution was complete, the reaction was recooled in a 0° C. ice bath, and benzyl bromide (18.4 μl, 0.16 mmol) was added. The reaction was warmed to room temperature and allowed to stir for 10 minutes. The slurry was partitioned between EtOAc (2 mL) and water (2 mL), the layers were separated, and the aqueous layer was reextracted twice with 2 mL of EtOAc. The organic layers were combined, washed once with brine, dried ($Na_2SO_4$), and concentrated under reduced pressure. Flash chromatography (1:1 Hexanes/EtOAc, then 10% MeOH in EtOAc) afforded 31 mg (95%) of (13) as white crystals. $[\alpha]^{25}=-57.7$ (c=0.052, $CHCl_3$); FTIR (neat) 1629, 1540, 1465, 1437, 1387, 1357, 737, 694 $cm^{-1}$; $^1H$ NMR (400 MHz, $CDCl_3$) δ 7.37–7.27 (m, 10H), 6.06 (d, J=9.3 Hz, 2H), 4.50 (d, J=12.0 Hz, 2H), 4.45 (d, J=12.0 Hz, 2H), 3.87–3.82 (m, 2H), 3.55 (dd, J=9.7, 4.0 Hz, 2H), 3.40 (dd, J=9.7, 4.2 Hz, 2H), 2.59–2.42 (m, 4H), 1.95–1.86 (m, 2H), 0.90 (d, J=7.0 Hz, 6H), 0.88 (d, J=7.0 Hz, 6H); $^{13}C$ NMR (100 MHz, $CDCl_3$) δ 171.74, 138.14, 128.39, 127.61, 127.65, 73.16, 70.03, 54.11, 32.04, 29.26, 19.49, 18.85; HRMS calculated for $C_{28}H_{41}N_2O_4$ $(M+H)^+$ required 469.3066, found 469.3076.

V. Preparation of Valine-Derived Diamine (14)

Lithium aluminum hydride (LAH) (316 mg, 8.3 mmol) was added to a solution of compound (13) (193 mg, 0.42 mmol) and dioxane (2 mL) at room temperature. The flask was equipped with a condenser and heated to reflux for 3 hours. The reaction was cooled to room temperature and quenched over a 30-minute period with water and Glauber's salt ($Na_2SO_4 \cdot 10 H_2O$). The reaction mixture was stirred for an additional 30 minutes and filtered over a pad of Celite (EtOAc). The solution was concentrated and subjected to flash chromatography ($SiO_2$, 10% MeOH in EtOAc) to afford 164 mg (91%) of (14) as a colorless oil. $[\alpha]^{25}=+5.8$ (c=1.36, $CHCl_3$); FTIR(neat) 1466, 1383, 1364, 735, 697 $cm^{-1}$; $^1H$ NMR (400 MHz, $CDCl_3$) δ 7.36–7.26 (m, 10H), 4.51 (s, 6H), 3.50 (dd, J=9.4, 4.4 Hz, 2H), 3.77 (dd, J=9.4, 6.8 Hz, 2H), 2.62–2.56 (m, 4H), 2.53 (dt, J=6.6, 4.7 Hz, 2H), 1.54–1.47 (m, 4H), 1.23 (bs, 2H), 0.91 (d, J=6.9 Hz, 6H), 0.89 (d, J=6.9 Hz, 6H); $^{13}C$ NMR (100 MHz, $CDCl_3$) δ 138.45, 128.27, 127.54, 127.45, 73.14, 70.33, 62.62, 48.00, 28.86, 28.36, 18.91, 18.25; HRMS calculated for $C_{28}H_{45}N_2O_2$ $(M+H)^+$ required 441.3481, found 441.3504.

Example 2

Scheme B depicts the reaction scheme of this example upon attempting to form a valine-derived cyclic phosphonamide (1).

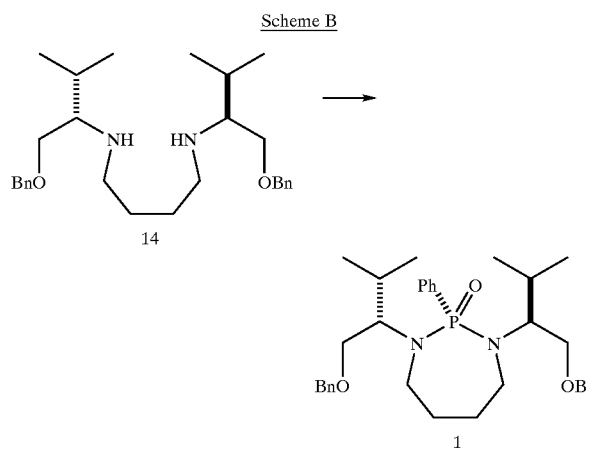

Scheme B

A solution of compound (14) (6.5 mg, 0.048 mmol) and $CH_2Cl_2$ (100 μl) was cooled in a 0° C. ice bath, and $Et_3N$ (23 μl, 0.17 mmol) was slowly added. Dichlorophenylphosphine (6.5 μl, 48.0 μmol) was dissolved in $CH_2Cl_2$ (100 μl) and added drop-wise over 1 minute. The reaction was warmed to room temperature for 5 minutes, then recooled in a 0° C. ice bath. Next, m-chloroperbenzoic acid (mCPBA) (17.7 mg, 0.072 mmol) was added to the salt slurry. After warming to room temperature, the reaction was concentrated under reduced pressure, and the slurry was subjected to flash chromatography (EtOAc) to afford 18.5 mg (75%) of (1) as a colorless oil. $[\alpha]^{25}=-54.1$ (c=0.15, $CHCl_3$);FTIR(neat) 1468, 1453, 1384, 1362, 1207 (P=O), 725, 698 $cm^{-1}$; $^1H$ NMR (400 MHz, $CDCl_3$) δ 7.92–7.69 (m, 2H), 7.41–7.24 (m, 13H), 4.61 (d, J=11.8 Hz, 1H), 4.37, (d, J =13.0 Hz, 1H), 4.36 (s, 2H), 3.77–3.67 (m, 2H), 3.66–3.58 (m, 1H), 3.53 (dd, J=10.0, 7.0 Hz, 1H), 3.47–3.38 (m, 2H), 3.34–3.17 (m, 3H), 2.92 (dddd, $J_{HH}$=14.2 Hz, $J_{HH}$=10.4 HZ, $J_{HH}$=7.0, 3.2 Hz, 1H), 1.98–1.87 (m, 2H), 1.78–1.54 (m, 4H), 1.01 (d, J=6.7 Hz, 3H), 0.80 (d, J=6.5 Hz, 3H), 0.80 (d, J=6.5 Hz, 3H), 0.44 (d, J=6.7 Hz, 3H); $^{13}C$ NMR (100 MHz, $CDCl_3$) d 138.70, 138.39, 133.71 (d, $J_{CP}$=145.7 Hz), 130.64 (d, $J_{CP}$=2.8 Hz), 128.27, 128.14, 127.73, 127.68, 127.60, 127.55, 127.51, 127.27, 73.09, 72.76, 71.57, 71.52, 62.46 (d, $J_{CP}$=7.0 Hz), 61.44 (d, $J_{CP}$=6.4 Hz), 42.23, 42.45, 29.32, 28.36, 27.14, 27.09, 21.42, 21.09. 20.37, 20.26; $^{31}P$ NMR (162 MHz, $CDCl_3$) δ 29.05; HRMS calculated for $C_{34}H_{48}N_2O_3P(M+H)^+$ required 563.3403, found 563.3417.

Example 3

Scheme C depicts the reaction scheme followed in Parts I–III of this example.

Scheme C

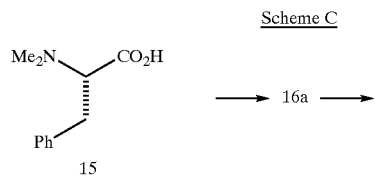

15

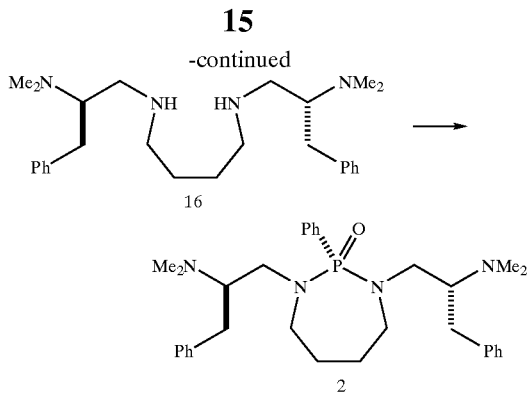

I. Preparation of Phenylalanine-Derived Diamide (16a)

N,N-dimethylphenylalanine (15) (1.19 g, 6.2 mmol), Et$_3$N (1.29 ml, 9.3 mmol), and 1,4-diamino butane (303 µl, 3.0 mmol) were dissolved in CH$_3$CN (50 mL). O-benzotriole-N,N,N',N'-tetramethyl-uronium-hexafluorophosphate (HBTU) was added, and the reaction mixture was stirred at room temperature for 30 minutes, and then concentrated under reduced pressure. The mixture was vacuum filtered (EtOAc), further concentrated under reduced pressure, and subjected to flash chromatography (EtOAc, then 10% Et$_3$N in EtOAc) to afford 1.06 g (80%, non-optimized) of (16a) as white crystals. $[\alpha]^{25}$–105.7 (c=0.19, CHCl$_3$); FTIR (neat) 1649, 1455, 1384, 748, 700 cm$^{-1}$; $^1$H NMR (400 MHz, CDCl$_3$) δ 7.19–7.16 (m, 8H), 6.89 (t, J=5.7 Hz, 2H), 6.40 (s, 1H), 5.90 (s, 1H), 3.13–3.04 (m, 6H), 3.12 (dd, J=12.7, 5.3 Hz, 2H), 2.79 (dd, J=13.4, 5.1 Hz, 2H), 2.23 (s, 12H), 1.24 (s, 4H); $^{13}$C NMR (100 MHz, CDCl$_3$) δ 171.68, 129.44, 128.88, 127.91, 125.69, 70.61, 41.91, 38.25, 32.84, 26.52; HRMS calculated for C$_{26}$H$_{39}$N$_4$O$_2$ (M+H)$^+$ required 439.3073, found 439.3074.

II. Preparation of Phenylalanine-Derived Diamine (16)

LAH (304 mg, 8.0 mmol) was added to a solution of compound (16a) (433 mg, 0.99 mmol) and dioxane (5 mL) at room temperature. The flask was equipped with a condenser and heated to reflux for 3 hours. The reaction was cooled to room temperature and quenched over a 30 minute period with water and Glauber's salt (Na$_2$SO$_4$·10 OH$_2$O). The reaction mixture was stirred for an additional 30 minutes, and filtered over a pad of Celite (CH$_2$Cl$_2$). The CH$_2$Cl$_2$ was washed with brine, dried (Na$_2$SO$_4$), and concentrated under reduced pressure to afford 338 mg (83%, non-optimized) of (16) as a colorless oil. $[\alpha]^{25}$=+18.8 (c=2.43, CHCl$_3$); FTIR (neat) 1495, 1454, 1373, 740, 699 cm$^{-1}$; $^1$H NMR (400 MHz, CDCl$_3$) δ 7.25–7.21 (m, 4H), 7.15–7.10 (m, 6H), 2.92–2.82 (m, 4H), 2.52–2.42 (m, 6H), 2.28 (s, 12H), 1.44–1.40 (m, 4H), 7.15–7.10 NMR (100 MHz, CDCl$_3$) δ 140.02, 128.94, 128.23, 125.71, 64.84, 49.50, 49.46, 40.05, 31.40, 27.63; HRMS calculated for C$_{26}$H$_{43}$N$_4$ (M+H)$^+$ required 411.3488, found 411.3495.

III. Preparation of Phenylalanine-Derived Cyclic Phosphonamide (2)

A solution of compound (16) (47 mg, 0.12 mmol) and CH$_2$Cl$_2$ (500 µl) was cooled in a 0° C. ice bath, and Et$_3$N (66 µl, 0.48 mmol) was added, and the mixture was stirred for 5 minutes. Dichlorophenylphosphine (19 µl, 0.14 mmol) was added, and the reaction was warmed briefly to room temperature, and then recooled in a 0° C. ice bath. Next, mCPBA (35 mg, 0.21 mmol) was added in one portion to the salt slurry. After warming to room temperature, the reaction was concentrated under reduced pressure and the slurry was subjected to flash chromatography (10% Et$_3$N in EtOAc, then 20% Et$_3$N in CH$_3$CN) to afford 48 mg (68%, non-optimized) of (2) as a colorless oil. $[\alpha]^{25}$=+18.5 (c=0.054, CHCl$_3$); FTIR (neat) 1453, 1437, 1378, 1201 (P=O), 737, 698 cm$^{-1}$; $^1$H NMR (400 MHz, CDCl$_3$) δ 7.83–7.78 (m, 2H), 7.52–6.96 (m, 133H), 3.29–2.92 (m, 6H), 2.84–2.55 (m, 5H), 2.35–2.27 (m, 3H), 2.18 (s, 6H), 2.06 (s, 6H), 1.8–1.48 (m, 4H); $^{13}$C NMR (100 MHz, CDCl$_3$) δ 140.93, 140.85, 132.37 (d, J$_{CP}$=8.5 Hz), 130.64, 129.59 (d, J$_{CP}$=212.0 Hz), 128.99, 128.85, 128.25, 128.11, 127.79 (d, J$_{CP}$=13.3 Hz), 125.61, 125.50, 65.25, 65.21, 64.79, 64.79, 64.76, 47.08, 46.94, 40.34, 40.29, 33.00, 32.36, 28.39, 28.02; 31P NMR (162 MHz, CDCl$_3$) δ 29.14; HRMS calculated for C$_{32}$H$_{46}$N$_4$OP (M+H)$^+$ required 533.3409, found 533.3427.

Example 4

Scheme D depicts the reaction scheme followed in Parts I–III of this example.

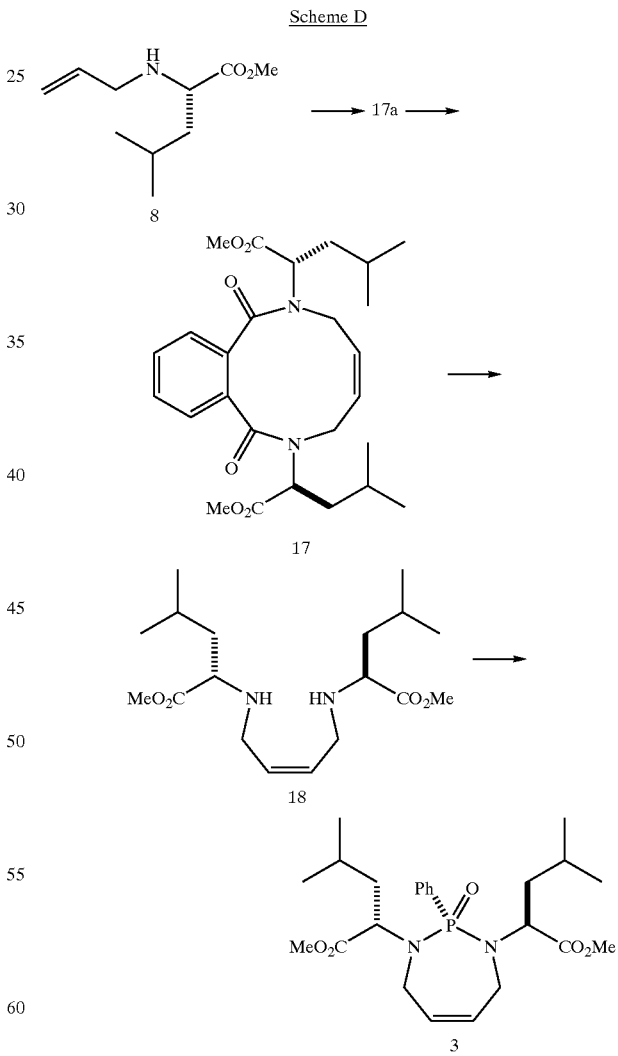

I. Preparation of Leucine-Derived Phthalic Diamide (17a) (as a Mixture of Rotamers A solution of allylated leucine methyl ester (8) (308 mg, 1.67 mmol), 4-dimethylaminopyridine (DMAP) (20 mg, 0.17 mmol), Et$_3$N (405 μl, 2.91 mmol) and CH$_2$Cl$_2$ (7 mL) was cooled in a 0° C. ice bath. Phthaloyl dichloride (120 μl, 0.83 mmol) was added drop-wise, and the slurry was warmed to room temperature. After 30 minutes, the reaction was partitioned between EtOAc (10 mL) and H$_2$O (10 mL), and the water layer was extracted twice with EtOAc (5 mL). The organic layers were combined, washed with brine, dried (Na$_2$SO$_4$), and concentrated under reduced pressure. Flash chromatography (2:1 Hexanes/EtOAc) afforded both a single spot (TLC) and a single peak (GC,97%) of 398 mg (96%) of (17a) as a mixture of rotamers. $[]^{25}$=−64.8 (c=0.66, CHCl$_3$); FTIR (neat) 1743, 1647, 1456, 1436, 1410, 754 cm$^{-1}$; $^1$H NMR (400 MHz, CDCl$_3$) δ 7.40–7.32 (m, 4H), 5.93–5.79 (m, 2H), 5.23–5.10 (m, 4H), 4.32 (bs, 2H), 3.97–3.87 (m, 2H), 3.78–3.68 (m, 8H), 2.11–1.60 (m, 6H), 0.96–0.70 (m, 12H), $^{13}$C NMR (100 MHz, CDCl$_3$) δ 171.97, 170.75, 136.44, 135.21, 129.07, 126.80, 117.83, 56.78, 52.10, 46.86, 38.74, 25.79, 23.18, 22.99; HRMS calculated for C$_{28}$H$_{41}$N$_2$O$_6$ (M+H)$^+$ required 501.2965, found 501.2971.

II. Preparation of Leucine-Derived Bicyclic Diamide (17)

A solution of compound (17a) (70 mg, 0.14 mmol) and CH$_2$Cl$_2$ (14 mL) was purged with argon gas for 5 minutes. The solution was brought to reflux and Grubbs catalyst (18 mg, 21.9 μmol) was added in three 6 mg portions over a 24-hour period. After 36 hours, the reaction was concentrated under reduced pressure and subjected to flash chromatography (1:1 Hexanes/EtOAc) to afford 64 mg (97%) of (17) as a colorless oil. $[\alpha]^{25}$=−43.6 (c=0.51, CHCl$_3$); FTIR (neat) 1741, 1650, 1430, 1412, 1367, 1331, 756 cm$^{-1}$; $^1$H NMR (400 MHz, CDCl$_3$) δ 7.46–7.44 (m, 2H), 7.39–7.37 (m, 1H), 7.31–7.28 (m, 1H), 5.85 (s, 1H), 5.75 (s, 1H), 5.09 (s, 1H), 4.35 (s, 1H), 4.09–4.01 (m, 1H), 3.96 (dd, J=15.2, 6.0 Hz, 1H), 3.75 (s, 3H), 3.75 (s, 3H), 3.70–3.57 (m, 2H), 2.20–2.13 (m, 1H), 1.98–1.86 (m, 1H), 1.75–1.61 (m, 4H), 1.00–0.96 (m, 12H); $^3$C NMR (100 MHz, CDCl$_3$) δ 172.25, 171.75, 169.93, 169.47, 134.62, 134.49, 131.59, 129.54, 129.42, 129.24, 127.44, 126.73, 56.92, 56.02, 52.18, 52.18, 45.66, 42.83, 39.27, 38.37, 25.36, 25.11, 22.76, 22.64, 22.30, 22.18; HRMS calculated for C$_{26}$H$_{37}$N$_2$O$_6$ (M+H)$^+$ required 473.2652, found 473.2646.

III. Preparation of Leucine-Derived Diamine (18)

In a sealable pyrex test tube, compound (17) (100 mg, 0.21 mmol) was dissolved in HCl saturated MeOH (3 mL), capped, and heated in a 115° C. oil bath. After 72 hours, the reaction mixture was cooled to room temperature and then concentrated under reduced pressure. EtOAc (2 mL) was added, and the reaction mixture was cooled in a 0° C. ice bath. Et$_3$N (1 mL) was added, and the reaction mixture was slowly warmed to room temperature and stirred for 1 hour. The reaction mixture was concentrated under reduced pressure and subjected to flash chromatography (1:1 Hexanes/EtOAc) to afford 24 mg (36%) of (18) as a colorless oil. $[\alpha]^{25}$=+12.0, (c=0.05, CHCl$_3$); FTIR (neat) 1737, 1468, 1433, 1368 cm$^{-1}$; $^1$H NMR (400 MHz, CDCl$_3$) δ 5.56 (dd, J=4.5, 4.5 Hz, 2H), 3.72 (s, 6H), 3.29–3.21 (m, 4H), 3.09 (dd, J=13.2, 4.8 Hz, 2H), 1.76–1.66 (m, 2H), 1.54 (bs, 2H), 1.47–1.43 (m, 4H), 0.92 (d, J=6.6 Hz, 6H), 0.89 (d, J=6.6 Hz, 6H); $^{13}$C NMR (100 MHz, CDCl$_3$) δ 176.44, 130.17. 59.34, 51.60, 44.62, 42.85, 24.90, 22.66, 22.35; HRMS calculated for C$_{18}$H$_{35}$N$_2$O$_4$ (M+H)$^-$ required 343.2597, found 343.2619.

IV Preparation of Leucine-derived cyclic phosphonamide (3)

Compound (18) (10.5 mg, 30.7 μmol), CH$_2$Cl$_2$ (1 mL), Et$_3$N (20 μl, 0.14 mmol), dichlorophenylphosphine (54 μl, 39.9 μmol) and mCPBA (12 mg, 0.05 mmol) afforded a slurry that was subjected to flash chromatography (EtOAc) to yield 12.3 mg (86%) of a colorless oil. $[\alpha]^{25}$=+108.3 (c=0.072, CHCl$_3$); FTIR (neat) 1731, 1430, 1388, 1368, 1204 (P=O), 748, 702 cm$^{-1}$; $^1$HNMR (400 MHz, CDCl$_3$) δ 7.86 (dd, J$_{HP}$=12.1 Hz, J$_{HH}$=6.8 Hz, 2H), 7.55–7.50 (m, 1H), 7.47–7.43 (m, 2H), 5.75–5.64 (m, 2H), 4.18 (ddd, J=9.1, 6.3, 6.3 Hz, 1H), 4.08 (ddd, J$_{HP}$=13.3 Hz, J$_{HH}$=5.8, 5.8 Hz, 1H), 4.02–3.81 (m, 3H), 3.76–3.70 (m, 1H), 3.68 (s, 3H), 3.46 (s, 3H), 1.78–1.66 (m, 2H), 1.65–1.57 (m, 2H), 1.55 (ddd, J=14.3, 7.2, 7.2 Hz, 1H), 1.40 (ddd, J=13.9, 6.3, 6.3 Hz, 1H), 0.90 (d, J=6.4 Hz, 3H), 0.86 (d, J=6.6 Hz, 3H), 0.73 (d, J=6.6 Hz, 3H), 0.68 (d, J=6.6 Hz, 3H); $^{13}$C NMR (100 MHz, CDCl$_3$) δ 173.49, 173.16, 132.71 (d, J$_{CP}$=9.0 Hz), 131.81, 131.78, 129.2 (d, J$_{CP}$=181.1 Hz), 128.23 (d, J$_{CP}$=13.4 Hz), 128.22, 56.43 (d, J$_{CP}$=7.0 Hz), 55.80 (d, J$_{CP}$=6.0 Hz), 51.88, 51.46, 41.37 (d, J$_{CP}$=2.8 Hz), 40.53 (d, J$_{CP}$=2.8 Hz), 39.47, 39.15 (d, J$_{CP}$=4.9 Hz), 24.62, 24.42, 22.97, 22.61, 22.30, 21.96; $^{31}$P NMR (162 MHz, CDCl$_3$) δ 29.56; HRMS calculated for C$_{24}$H$_{38}$N$_2$O$_5$P (M+H)$^+$ required 465.2518, found 465.2521.

Example 5

Scheme E depicts the reaction scheme followed in this example to prepare valine-derived phosphonamidic dichloridate (10).

Scheme E

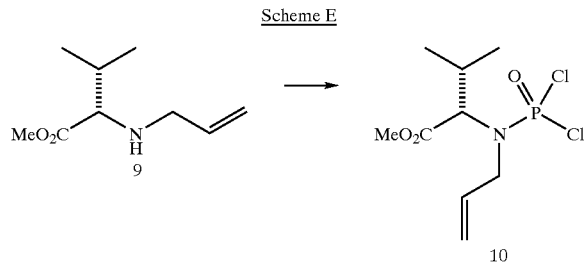

A solution of POCl$_3$ (1.14 g, 7.45 mmol) and CH$_2$Cl$_2$ (7.5 mL) was cooled in a 0° C. ice bath. Next, Et$_3$N (2.26 g, 22.35 mmol) and DMAP (46 mg, 0.37 mmol) were added slowly, and the solution was warmed to room temperature and stirred for 15 minutes. Allylated valine methyl ester (9) (1.40 g, 8.19 mmol) was added, and the reaction was brought to reflux and stirred overnight. The reaction was concentrated under reduced pressure and partitioned between EtOAc (25 mL) and water (25 mL). The layers were separated, and the aqueous layer was washed with EtOAc (3×5 mL). The organic layers were combined, washed with brine, dried (Na$_2$SO$_4$), and further concentrated under reduced pressure. Flash chromatography (10:1 Hexanes/EtOAc) afforded 1.61 g (75%) of (10) as a colorless oil. $[\alpha]^{25}$=−44.9 (c=0.55, CHCl$_3$); FTIR (neat) 1745, 1437, 1373, 1276 (P=O) cm$^{-1}$; $^1$H NMR (400 MHz, CDCl$_3$) δ 5.86 (dddd, J=16.8, 10.1, 6.6, 6.6 Hz, 1H), 5.26 (dd, J=17.0, 0.8 Hz, 1H), 5.20 (d, J=10.1 Hz, 1H), 3.99–3.75 (m, 2H), 3.96 (dd, J$_{HH}$=18.0 Hz, J$_{HP}$=10.6 Hz, 1H), 3.71 (s, 3H), 2.39–2.27 (m, 1H), 0.98 (d, J=6.6 Hz, 3H), 0.95 (d, J=6.6 Hz, 3H); $^{13}$C NMR (100 MHz, CDCl$_3$) δ 170.48 (d, J$_{CP}$=3.1 Hz), 132.48 (d, J$_{CP}$=2.5 Hz), 119.63, 65.73 (d, J$_{CP}$=2.1 Hz), 51.96, 48.44 (d, J$_{CP}$=4.6 Hz), 27.70 (d, J$_{CP}$=4.2 Hz), 19.70, 19.60; $^{31}$P NMR (162 MHz, CDCl$_3$) δ 19.57; HRMS calculated for C$_9$Hl$_7$Cl$_2$NO$_3$P (M+H)$^+$ required 288.0323, found 288.0337.

Example 6

Scheme F depicts the reaction schemes followed in Parts I–IV of this example.

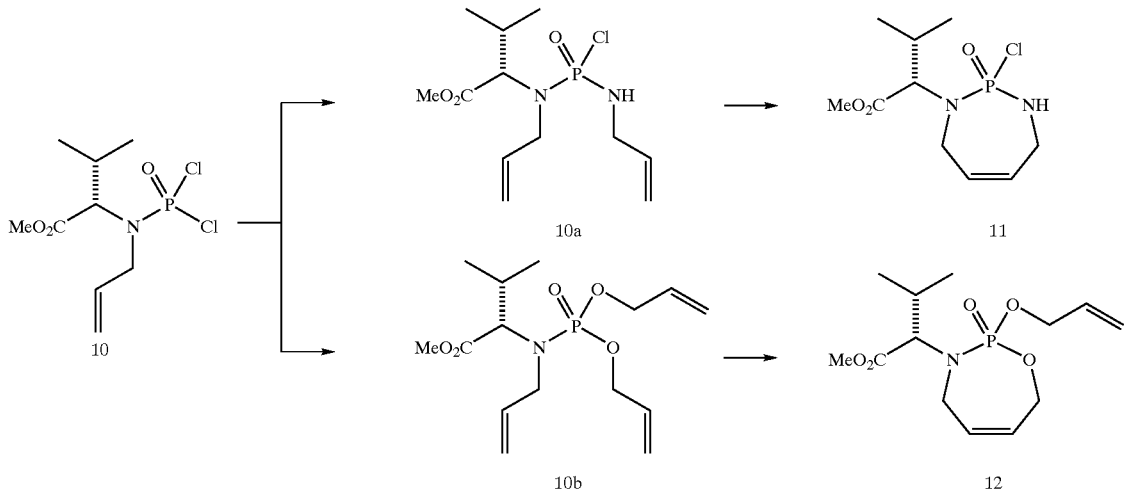

Scheme F

I. Preparation of Valine-Derived Acyclic Phosphonamidic Chloridate (10a)

A solution of compound (10) (499 mg, 1.73 mmol) and CH$_2$Cl$_2$ (3.5 mL) was cooled in a 0° C. ice bath. Next, Et$_3$N (526 mg, 5.20 mmol) and DMAP (21 mg, 0.17 mmol) were added slowly, and the solution was warmed to room temperature, stirred for 15 minutes, then cooled in a –78° C. acetone/CO$_2$(s) bath. Allyl amine (99 mg, 1.73 mmol) was added drop-wise, and the reaction slowly warmed to room temperature over the course of 12 hours. The crude reaction mixture was partitioned between CH$_2$Cl$_2$ (25 mL) and water (25 mL), the layers were separated, and the aqueous layer was washed with CH$_2$Cl$_2$ (3×5 mL). The organic layers were combined, washed with brine, dried (Na$_2$SO$_4$), and concentrated under reduced pressure. Flash chromatography (4:1 Hexanes/EtOAc, then 2:1 Hexanes/EtOAc) afforded 144 mg (27%) of (10a) as a mixture of inseparable diastereomers (ds=3.8:1.0 as determined by $^{31}$P NMR) as a yellow oil. FTIR (neat) 1740, 1435, 1371, 1231 (P=O) cm$^{-1}$; $^1$H NMR (400 MHz, CDCl$_3$) δ 5.94–5.80 (m, 4H), 5.25–5.12 (m, 8H), 4.02–3.73 (m, 5H), 3.70 (s, 3H), 3.69 (s, 3H), 3.67–3.59 (m, 7H), 2.32–2.20 (m, 2H), 1.01 (d, J=6.6 Hz, 3H), 1.00 (d, J=6.4 Hz, 3H), 0.93 (d, J=6.5 Hz, 3H), 0.92 (d, J=6.5 Hz, 3H); $^{13}$C NMR (100 MHz, CDCl$_3$) δ 171.93, 171.91, 134.86, 134.86, 134.77, 134.77, 118.15, 118.15, 116.55, 116.50, 64.91 (d, J$_{CP}$=3.3 Hz), 64.67 (d, J$_{CP}$=3.0 Hz), 51.80, 25.05; HRMS calculated for C$_{12}$H$_{23}$ClN$_2$O$_3$P (M+H)$^+$ required 309.1135, found 309.1125.

II. Preparation of Cyclic Phosphonamidic Chloridate (11) Diastereomers

A solution of compound (10a) (105 mg, 0.34 mmol) and CH$_2$Cl$_2$ (12 mL) was purged with argon for 10 minutes. Grubbs Catalyst 1 (8 mg, 10 μmol) was added, and the solution was brought to reflux and monitored by TLC. The reaction was concentrated under reduced pressure and subjected to flash chromatography (3:1 Hexanes/EtOAc, then 2:1 Hexanes/EtOAc) to afford 36 mg (38%) of one diastereomer (11a) and 14 mg (15%) of the other diastereomer (11b), both as white solids.

Characterization of the single diastereomer (11a) was as follows: mp 87–88° C.; R$_f$=0.46 (1:2 Hexanes/EtOAc); [α]$^{25}$=−87.6 (c=0.45, CHCl$_3$); FTIR (neat) 1737, 1450, 1436, 1370, 1249 (P=O) cm$^{-1}$; $^1$H NMR (400 MHz, CDCl$_3$) δ 5.75–5.71 (m, 1H), 5.61–5.57 (m, 1H), 4.01–3.73 (m, 3H), 3.99 (dd, J$_{HH}$=10.1 Hz, J$_{HP}$=10.1 Hz, 1H), 3.71 (s, 3H), 3.68–3.42 (m, 2H), 2.12–2.03 (m, 1H), 1.00 (d, J=6.7 Hz, 3H), 0.92 (d, J=6.6 Hz, 3H); $^{13}$C NMR (100 MHz, CDCl$_3$) δ 171.75, 128.20, 127.19, 64.24 (d, J$_{CP}$=2.1 Hz), 51.62, 40.69 (d, J$_{CP}$=3.7 Hz), 40.16, 28.34 (d, J$_{CP}$=6.9 Hz), 19.20, 19.01; $^{31}$P NMR (162 MHz, CDCl$_3$) δ 27.41; HRMS calculated for C$_{10}$H$_{19}$ClN$_2$O$_5$P (M+H)$^+$ required 281.0822, found 281.0815.

Characterization of the single diastereomer (11b) was as follows: mp 115–117° C.; R$_f$=0.32 (1:2 Hexanes/EtOAc); [α]$^{25}$=−37.4 (c=0.19, CHCl$_3$); FTIR (neat) 1738, 1469, 1437, 13 89, 1241 (P=O) cm$^{-1}$; $^1$H NMR (400 MHz, CDCl$_3$) δ 5.65–5.60 (m, 1H), 5.55–5.50 (m, 1H), 4.04–3.88 (m, 2H), 4.02 (dd, J=11.4 Hz, J$_{HP}$=11.4 Hz, 1H), 3.66 (s, 3H), 3.64–3.39 (m, 3H), 2.27–2.17 (m, 1H), 0.98 (d, J=6.8 Hz, 3H), 0.92 (d, J=6.5 Hz, 3H); $^{13}$C NMR (100 MHz, CDCl$_3$) δ 171.80 (d, J$_{CP}$=7.9 Hz), 127.40, 127.22, 63.94 (d, J$_{CP}$=4.0 Hz), 51.78, 39.77, 39.67 (d, J$_{CP}$=5.1 Hz), 26.72, 19.37, 19.22; $^{31}$P NMR (162 MHz, CDCl$_3$) δ 27.81; HRMS calculated for C$_{10}$H$_{19}$ClN$_2$O$_5$P (M+H)$^+$ required 281.0822, found 281.0831.

III. Preparation of Valine-Derived Acylcic Bis-Allyloxyphosphonamidate (10b)

A solution of allyl alcohol (210 mg, 3.61 mmol) and THF (1.8 mL) was cooled in a 0° C. ice bath. Sodium bis(trimethylsilyl)amide (3.5 mL of 1.0 M solution in THF) was added, and the solution was warmed to room temperature and stirred for 30 minutes. In separate flask, a solution of (10) (506 mg, 1.76 mmol) and THF (1.8 mL) was cooled in a –10° C. (NaCl saturated) ice bath. The allyloxide solution was cannulated into the solution of (10) at –10° C., and the solution was stirred for 1 hour. The reaction was quenched with NH$_4$Cl (aq) and concentrated under reduced pressure. The crude reaction mixture was partitioned between EtOAc (25 mL) and water (25 mL), the layers were separated, and the aqueous layer was washed with EtOAc (3×5 mL). The organic layers were combined, washed with brine, dried (Na$_2$SO$_4$), and further concentrated under reduced pressure. Flash chromatography (6:1 Hexanes/EtOAc, then 5:1 Hexanes/EtOAc) afforded 401 mg (69%) of (10b) as a colorless oil. TLC R$_f$=0.46 (1:1 Hexanes/EtOAc); [α]$^{25}$=–25.7 (c=0.46, CHCl$_3$); FTIR (neat) 1738, 1434, 1370, 1262 (P=O) cm$^{-1}$; $^1$H NMR (400 MHz, CDCl$_3$) δ 5.98–5.88 (m, 2H), 5.84 (dddd, J=16.8, 10.1, 6.6, 6.6 Hz, 1H), 5.36–5.31 (m, 2H), 5.23–5.20 (m, 2H), 5.14 (dd, J=17.1, 1.2 Hz, 1H), 5.05 (d, J=10.1 Hz, 1H), 4.60–4.41 (m, 4H), 3.80 (dd, J$_{HH}$=11.4 Hz, J$_{HP}$=11.4 Hz, 1H), 3.81–3.58 (m, 2H), 3.68 (s, 3H), 2.31–2.19 (m, 1H), 1.00 (d, J=6.7 Hz, 3H), 0.91 (d, J=6.5 Hz, 3H); $^{13}$C NMR (100 MHz, CDCl$_3$) δ 172.42 (d, J$_{CP}$=3.2 Hz), 135.66, 133.08 (d, J$_{CP}$=7.2 Hz), 133.01 (d, J$_{CP}$=7.5 Hz), 117.37, 117.33, 117.00, 67.01 (d, J$_{CP}$=5.4 Hz), 66.68 (d, J$_{CP}$=5.0 Hz), 64.85 (d, J$_{CP}$=4.9 Hz), 51.23, 46.63 (d, J$_{CP}$=3.4 Hz), 27.44 (d, J$_{CP}$=3.4 Hz), 19.82, 19.23; $^{31}$P NMR (162 MHz, CDCl$_3$) δ 10.95; HRMS calculated for C$_{15}$H$_{27}$NO$_5$P (M+H)$^+$ required 332.1627, found 332.1614.

IV. Preparation of Cyclic bis-allyloxyphosphonamidate (12) Diastereomers

A solution of (10b) (43 mg, 0.13 mmol) and CH$_2$Cl$_2$ (7 mL) was purged with argon for 10 minutes. Grubbs Catalyst 1 (3 mg, 4 μmol) was added, and the solution was brought to reflux and monitored by TLC. The reaction was concentrated under reduced pressure and subjected to flash chromatography (4:1, then 2:1 Hexanes/EtOAc) to afford 23 mg (59%) of one diastereomer (12a) and 16 mg (41%) of the other diastereomer (12b), both as colorless oils.

Characterization of the single diastereomer (12a) was as follows: R$_f$=0.54 (1:2 Hexanes/EtOAc); [α]$^{25}$=–10.7 (c=0.15, CHCl$_3$); FTIR (neat) 1737, 1457, 1394, 1263 (P=O) cm$^{-1}$; $^1$H NMR (400 MHz, CDCl$_3$) δ 5.92 (dddd, J=15.9, 10.6, 5.4, 5.4 Hz, 1H), 5.79–5.75 (m, 1H), 5.63 (dddd, J=11.5, 4.7, 2.2, 2.2 Hz, 1H), 5.33 (ddd, J=17.0, 3.0, 1.5 Hz, 1H), 5.21 (dd, J=10.5, 1.2 Hz, 1H), 4.99–4.92 (m, 1H), 4.55–4.52 (m, 2H), 4.48–4.36 (m, 1H), 3.88 (dd, J$_{HH}$=9.9 Hz, J$_{HP}$=9.9 Hz, 1H), 3.88–3.63 (m, 2H), 3.69 (s, 3H), 2.11–2.02 (m, 1H), 1.03 (d, J=6.6 Hz, 3H), 0.91 (d, J=6.6 Hz, 3H); $^{13}$C NMR (100 MHz, CDCl$_3$) δ 172.42, 133.02 (d, J$_{CP}$=7.4 Hz), 128.66, 125.91, 117.23, 67.37 (d, J$_{CP}$=5.5 Hz), 64.49 (d, J$_{CP}$=4.3 Hz), 63.81 (d, J$_{CP}$=4.8 Hz), 51.50, 40.40 (d, J$_{CP}$=3.0 Hz), 28.30 (d, J$_{CP}$=5.5 Hz), 19.23, 19.09; $^{31}$P NMR (162 MHz, CDCl$_3$) δ 15.04; HRMS calculated for C$_{13}$H$_{23}$NO$_5$P (M+H)$^+$ required 304.1314, found 304.1335.

Characterization of the single diastereomer (12b) was as follows: R$_f$=0.51 (1:2 Hexanes/EtOAc); [α]$^{25}$=+17.5 (c=0.04, CHCl$_3$); FTIR (neat) 1737, 1462, 1370, 1264 (P=O) cm$^{-1}$; $^1$H NMR (400 MHz, CDCl$_3$) δ 5.94 (dddd, J=16.1, 10.6, 5.4, 5.4 Hz, 1H), 5.65–5.60 (m, 1H), 5.55 (dddd, J=11.4, 4.7, 2.1, 2.1 Hz, 1H), 5.34 (ddd, J=17.2, 3.0, 1.4 Hz, 1H), 5.22 (dd, J=10.4, 1.3 Hz, 1H), 4.94–4.87 (m, 1H), 4.59–4.55 (m, 2H), 4.35 (ddd, J$_{HH}$=25.7 Hz, J$_{HP}$=16.0 Hz, J$_{HH}$=5.0 Hz, 1H), 3.89 (dd, J$_{HH}$=11.0 Hz, J$_{HP}$=11.0 Hz, 1H), 3.92–3.83 (m, 1H), 3.64 (s, 3H), 3.50 (ddd, J$_{HH}$=23.7 Hz, J$_{HH}$=17.8 Hz, J$_{HH}$=6.2 Hz, 1H), 2.24–2.13 (m, 1H), 0.96 (d, J=6.8 Hz, 3H), 0.89 (d, J=6.5 Hz, 3H); $^{13}$C NMR (100 MHz, CDCl$_3$) δ 172.18 (d, J$_{CP}$=5.6 Hz), 133.01 (d, J$_{CP}$=7.4 Hz), 128.95, 125.37, 117.52, 67.74 (d, J$_{CP}$=5.2 Hz), 64.11 (d, J$_{CP}$=5.6 Hz), 62.98 (d, J$_{CP}$=4.6 Hz), 51.60, 39.60 (d, J$_{CP}$=3.7 Hz), 26.70, 19.30, 18.83; $^{31}$P NMR (162 MHz, CDCl$_3$) δ 15.39; HRMS calculated for C$_{13}$H$_{23}$NO$_5$P (M+H)$^+$ required 304.1314, found 304.1296.

Example 7

Scheme G depicts the reaction schemes followed in Parts I–III of this example.

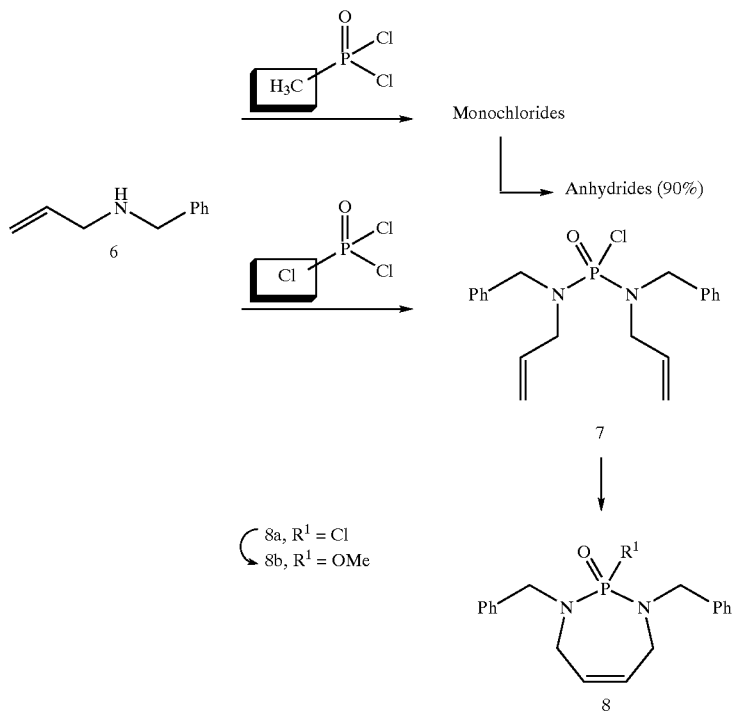

I. Preparation of Acyclic Phosphonamidic Chloridate (7)

A solution of $POCl_3$ (165 mg, 1.08 mmol) and $CH_2Cl_2$ (1.4 mL) was cooled in a 0° C. ice bath. Next, $Et_3N$ (708 mg, 6.99 mmol) and DMAP (13 mg, 0.11 mmol) were added slowly, and the solution was warmed to room temperature and stirred for 15 minutes. Benzyl allyl amine (6) (325 mg, 2.21 mmol) was added, and the reaction mixture was brought to reflux and stirred overnight. The crude reaction mixture was partitioned between $CH_2Cl_2$ (20 mL) and water (20 mL), the layers were separated, and the aqueous layer was washed with $CH_2Cl_2$ (3×5 mL). The organic layers were combined, washed with brine, dried ($Na_2SO_4$), and concentrated under reduced pressure. Flash chromatography (10:1 Hexanes/EtOAc) afforded 332 mg (82%) of (7) as a yellow oil. FTIR (neat) 1641, 1242(P=O), 735,699 $cm^{-1}$; $^1HNMR$ (400 MHz, $CDCl_3$) δ 67.36–7.26 (m, 10H), 5.82 (dddd, J=16.7, 10.2, 6.5, 6.5 Hz, 2H), 5.25 (d, J=10.1 Hz, 2H), 5.14 (dd, J=17.1, 1.4 Hz, 2H), 4.39 (dd, $J_{HH}$=15.1 Hz, $J_{HH}$=12.1 Hz, 2H), 4.32 (dd, $J_{HH}$=15.2 Hz, $J_{HH}$=11.0 Hz, 2H), 3.63–3.58 (m, 4H); $^{13}C$ NMR (100 MHz, $CDCl_3$) δ 136.37 (d, $J_{CP}$=4.4 Hz), 132.81 (d, $J_{CP}$=2.8 Hz), 128.63, 128.57, 127.64, 119.56, 48.94 (d, $J_{CP}$=4.5 Hz), 48.17 (d, $J_{CP}$=3.7 Hz); $^{31}P$ NMR (162 MHz, $CDCl_3$) δ 29.14; HRMS calculated for $C_{20}H_{25}ClN_2OP$ $(M+H)^+$ required 375.1393, found 375.1391.

II. Preparation of Cyclic phosphonamidic chloride (8a)

A solution of compound (7) (160 mg, 0.43 mmol) and $CH_2Cl_2$ (15 mL) was purged with argon for 10 minutes. Grubbs Catalyst 1 (11 mg, 13 µmol) was added, and the solution was brought to reflux for 45 minutes and monitored by TLC. The reaction was concentrated under reduced pressure and subjected to flash chromatography (8:1 Hexanes/EtOAc, then 4:1 Hexanes/EtOAc) to afford 147 mg (99%) of (8a) as a yellow oil. FTIR (neat) 1243 (P=O), 765, 720,697 $cm^4$; $^1H$ NMR (400 MHz, $CDCl_3$) δ 7.38–7.28 (m, 10H), 5.51 (dd, J=2.4, 2.4 Hz, 2H), 4.47 (dd, $J_{HH}$=15.4 Hz, $J_{HP}$=10.2 Hz, 2H), 4.36 (dd, $J_{HH}$=15.4 Hz, $J_{HP}$=10.2 Hz, 2H), 3.79 (ddd, $J_{HP}$=17.9 Hz, $J_{HH}$=17.9, 2.1 Hz, 2H), 3.60 (ddd, $J_{HH}$=18.5 Hz, $J_{HH}$=16.4 Hz, $J_{HH}$=2.2 Hz, 2H); $^{13}C$ NMR (100 MHz, $CDCl_3$) δ 137.13 (d, $J_{CP}$=5.5 Hz), 128.50, 127.95, 127.52, 126.90, 52.29 (d, $J_{CP}$=5.2 Hz), 44.89 (d, $J_{CP}$=4.5 Hz); $^{31}P$ NMR (162 MHz, $CDCl_3$) δ 32.52; HRMS calculated for $C_{18}H_{21}ClN_2OP$ $(M+H)^+$ required 347.1080, found 347.1098.

III. Preparation of Ayclic phosphonamide (8b)

A solution of MeOH (11 mg, 0.35 mmol) and THF (88 µL) was cooled in a 0° C. ice bath. Sodium bis(trimethylsilyl)amide (175 µL of 1.0 M solution in THF) was added, and the solution was warmed to room temperature and stirred for 15 minutes. In a separate flask, a solution of compound (8a) (60 mg, 0.17 mmol) and THF (88 µL) was cooled in a 0° C. ice bath. The sodium methoxide solution was cannulated into the solution of compound (8a) at 0° C., and the solution was warmed to room temperature and stirred for 2 hours. The crude reaction mixture was partitioned between EtOAc (10 mL) and water (10 mL), the layers were separated, and the aqueous layer was washed with EtOAc (3×2 mL). The organic layers were combined, dried ($Na_2SO_4$), and concentrated under reduced pressure. Flash chromatography (3:1 Hexanes/EtOAc, then 1:2 Hexanes/EtOAc) afforded 58 mg (100%) of (8b) as a yellow oil. FTIR (neat) 1454, 1358, 1231 (P=O), 761, 725, 697, 670 $cm^{-1}$; $^1H$ NMR(400 MHz, $CDCl_3$) δ 7.37–7.24 (m, 10H), 5.50 (dd, J=2.3, 2.3 Hz, 2H), 4.48 (dd, $J_{HH}$=15.3 Hz, $J_{HP}$=9.1 Hz, 2H), 4.08 (dd, $J_{HH}$=15.3 Hz, $J_{HP}$=5.9 Hz, 2H), 3.78 (d, $J_{HP}$=11.0 Hz, 3H), 3.60 (ddd, $J_{HP}$=17.6 HZ, $J_{HH}$=17.6, 2.3 Hz, 2H), 3.49 (ddd, $J_{HP}$=17.7 Hz, $J_{HH}$=17.7, 2.3

Hz, 2H); $^{13}$C NMR (100 MHz, CDCl$_3$) δ 138.82 (d, J$_{CP}$=4.6 Hz), 128.40, 127.92, 127.36, 127.15, 52.49 (d, J$_{CP}$=5.0 Hz), 51.43 (d, J$_{CP}$=4.0 Hz), 43.55 (d, J$_{CP}$=5.6 Hz); $^{31}$P NMR (162 MHz, CDCl$_3$) δ 22.99; HRMS calculated for C$_{19}$H$_{24}$N$_2$O$_2$P (M+H)$^+$ required 343.1575, found 343.1579.

Example 8

Scheme H depicts the reaction schemes followed in Parts I–II of this example.

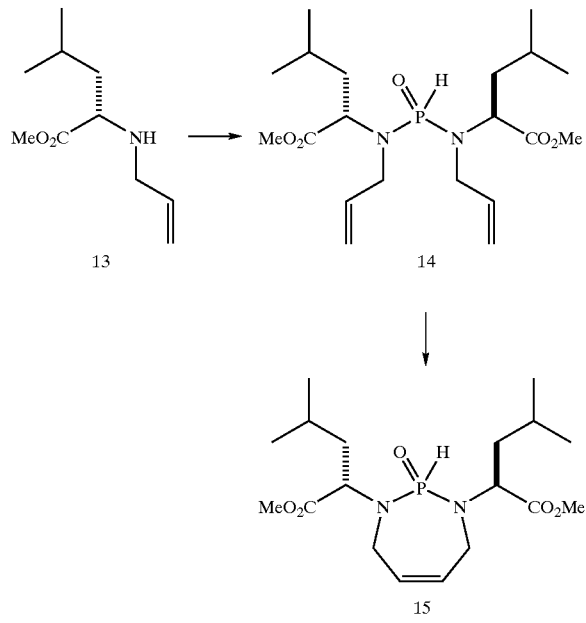

I. Preparation of Acyclic Leucine-Derived Phosphonamide (14)

A solution of PCl$_3$ (50 μL, 0.57 mmol) and Et$_2$O (5 mL) was cooled in a −10° C. (NaCl saturated) ice bath. Allylated leucine methyl ester (13) (477 mg, 2.58 mmol) in Et$_2$O (2 mL) was added via cannulae. After addition, the solution was warmed to reflux and heated overnight. The reaction was concentrated under reduced pressure and subjected to flash chromatography (1:1 Hexanes/EtOAc) to afford 112 mg (47%) of (14) as a colorless oil. [α]$^{25}$=+8.9 (c=0.12, CHCl$_3$); FTIR (neat) 1740, 1436, 1369, 1219 (P=O) cm$^{-1}$; $^1$H NMR(400 MHz, CDCl$_3$) δ 6.99 (d, J$_{HP}$=593.4 Hz, 1H), 5.83–5.72 (m, 2H), 5.16–5.01 (m, 4H), 4.18–4.08 (m, 2H), 3.74–3.53 (m, 4H), 3.65 (s, 3H), 3.64 (s, 3H), 1.75–1.64 (m, 6H), 0.91–0.88 (m, 12H); $^{13}$C NMR (100 MHz, CDCl$_3$) δ 173.55 (d, J$_{CP}$=2.2 Hz), 173.44 (d, J$_{CP}$=4.2 Hz), 135.84 (d, J$_{CP}$=2.2 Hz), 135.47 (d, J$_{CP}$=2.5 Hz), 117.64, 117.06, 55.31 (d, J$_{CP}$=4.9 Hz), 55.64 (d, J$_{CP}$=7.3 Hz), 51.82, 51.82, 46.91 (d, J$_{CP}$=5.9 Hz), 45.17 (d, J$_{CP}$=4.4 Hz), 39.91 (d, J$_{CP}$=3.0 Hz), 37.95 (d, J$_{CP}$=3.0 Hz), 24.61, 24.08, 22.76, 22.58, 21.84, 21.40; $^{31}$P NMR (100 MHz, CDCl$_3$) δ 21.92; HRMS calculated for C$_{20}$H$_{38}$N$_2$O$_5$P (M+H)$^+$ required 417.2518, found 417.2525.

II. Preparation of Cyclic Leucine-Derived Phosphonamide (15)

A solution of compound (14) (101 mg, 0.24 mmol) and CH$_2$Cl$_2$ (50 mL) was purged with argon gas for 10 minutes. Grubbs Catalyst 1 (7.4 mg, 7.5 μmol) was added in one portion, and the reaction was heated to reflux and monitored by TLC. The reaction was concentrated under reduced pressure and subjected to flash chromatography (1:1 Hexanes/EtOAc) to afford 93 mg (99%) of (15) as a colorless oil. [α]$^{25}$=−42.8 (c=1.55, CHCl$_3$); FTIR (neat) 1738, 1457, 1387, 1369, 1227 (P=O) cm$^{-1}$; $^1$H NMR (400 MHz, CDCl$_3$) δ 7.02 (d, J$_{HH}$=592.1 Hz, 1H), 5.54 (s, 2H), 4.28 (ddd, J$_{HP}$=10.2, J$_{HH}$=5.9 Hz, 5.9 Hz, 1H), 4.03–3.96 (m, 2H), 3.77–3.69 (m, 1H), 3.65 (s, 3H), 3.64 (s, 3H), 3.56–3.41 (m, 2H), 1.70–1.54 (m, 6H), 0.92 (d, J=6.4 Hz, 3H), 0.90–0.87 (m, 9H); $^{13}$C NMR (100 MHz, CDCl$_3$) δ 173.47 (d, J$_{CP}$=2.62 Hz), 172.90, 128.10, 127.79, 56.35 (d, J$_{CP}$=9.0 Hz), 56.16 (d, J$_{CP}$=6.9 Hz), 52.09, 52.02, 40.17 (d, J$_{CP}$=3.5 Hz), 40.04 (d, J$_{CP}$=5.2 Hz), 39.23 (d, J$_{CP}$=5.4 Hz), 38.20 (d, J$_{CP}$=3.3 Hz), 24.59, 24.55, 23.30, 22.96, 21.81, 21.38; $^{31}$P NMR (162 MHz, CDCl$_3$) δ 24.79; HRMS calculated for C$_{18}$H$_{34}$N$_2$OP (M+H)$^+$ required 389.2205, found 389.2206.

Example 9

Scheme I depicts the reaction schemes followed in Parts 1–111 of this example.

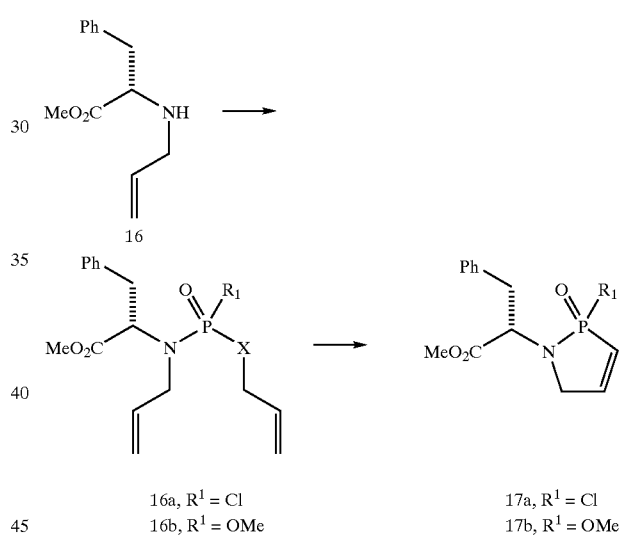

I. Preparation of Phenylalanine-Derived Vinyl Phosphonamidic Monochloridate (16a)

A solution of vinylphosphonic dichloride (345 mg, 2.38 mmol) and CH$_2$Cl$_2$ (10 mL) was cooled in a −10° C. (NaCl saturated) ice bath. Next, Et$_3$N (827 μL, 5.95 mmol) was added slowly, followed by the addition of allylated phenylalanine methyl ester (16) (471 mg, 2.14 mmol), and the mixture was warmed to reflux. The reaction was concentrated under reduced pressure and subjected to flash chromatography (2:1 Hexanes/EtOAc) to afford 703 mg (99%) of (16a) as a mixture of inseparable diastereomers as a colorless oil. FTIR (neat) 1741, 1437, 1397, 1240 (P=O), 751, 701 cm$^{-1}$; $^1$H NMR (400 MHz, CDCl$_3$) δ 7.30–7.19 (m, 10H), 6.27–5.89 (m, 6H), 5.63 (dddd, J=17.0, 10.1, 6.3, 6.3 Hz, 1H), 5.57 (dddd, J=16.9, 10.1, 6.6,6.6 Hz, 1H), 5.19–5.11 (m, 4H), 4.66 (ddd, J$_{HH}$=15.1 Hz, J$_{HH}$=9.6 Hz, J$_{HH}$=6.2 Hz, 1H), 4.49 (ddd, J$_{HH}$=15.9 Hz, J$_{HH}$=9.8 Hz, J$_{HH}$=6.1 Hz, 1H), 3.70 (s, 3H), 3.70 (s, 3H), 3.67–3.44 (m, 4H), 3.38 (ddd, J$_{HH}$=14.7,6.0 Hz, J$_{HH}$=6.0 Hz, 2H), 3.13 (m, 2H); $^{13}$C NMR (100 MHz, CDCl$_3$) δ 171.63, 171.43 (d, J$_{CP}$=5.3 Hz), 136.98, 136.96, 134.45, 134.29, 133.44 (d, J$_{CP}$=4.4 (d, J$_{CP}$=4.4 Hz), 133.37 (d, J$_{CP}$=2.9 Hz), 130.44 (d, J$_{CP}$=159.3 Hz), 130.41 (d, J$_{CP}$=158.6 Hz), 129.32, 129.17, 128.39, 128.36, 126.71, 126.64, 118.87, 118.87, 59.46 (d, J$_{CP}$=1.9 Hz), 58.46, 52.14, 52.14, 48.19 (d, J$_{CP}$=5.0 Hz), 47.50 (d, J$_{CP}$=5.2 Hz), 35.88, 35.75 (d, J$_{CP}$=4.2 Hz); $^{31}$P NMR (162 MHz, CDCl$_3$) δ 37.78, 36.95; HRMS calculated for C$_{15}$H$_{20}$ClNO$_3$P (M+H)$^+$ required 328.0869, found 328.0868.

II. Preparation of Cyclic Phosphonamidic Monochloridates (17a)

A solution of compound (16) (211 mg, 0.64 mmol) and CH$_2$Cl$_2$ (20 mL) was purged with argon gas for 10 minutes. Grubbs Catalyst 1 (1.6 mg, 19.2 μmol) was added and the reaction was heated to reflux and monitored by TLC. The reaction was concentrated under reduced pressure and subjected to flash chromatography (2:1 Hexanes/EtOAc) to afford 187 mg (98%) of (17a) as a separable mixture of two diastereomers (17a, and 17a), both as colorless oils.

Characterization of the isolated diastereomer (17a$_1$) was as follows: R$_f$=0.30 (1:1 Hexanes/EtOAc); [α]$^{25}$=+13.4; (c=0.15, CHCl$_3$); FTIR (neat) 1736, 1455, 1385, 1253 (P=O), 750, 692 cm$^{-1}$; $^1$H NMR (400 MHz, CDCl$_3$) δ 7.30–7.21 (m, 5H), 7.08 (dddd, J$_{HP}$=50.0, J$_{HH}$=8.8, 1.9, 1.9 Hz, 1H), 6.29 (dddd, J$_{HP}$=35.0 Hz, J$_{HH}$=8.8, 2.1, 2.1 Hz, 1H), 4.58 (ddd, J$_{HH}$=7.7, 7.7 Hz, J$_{HH}$=7.7 Hz, 1H), 3.34 (ddd, J$_{HH}$=17.6, 2.0 Hz, J$_{HP}$=2.0 Hz, 1H), 3.98 (dddd, J$_{HH}$=17.8, 15.7, 2.2 Hz, J$_{HP}$=2.2 Hz, 1H), 3.34 (s, 3H), 3.30 (dd, J=14.0, 8.1 Hz, 1H), 3.09 (dd, J=14.0, 7.7 Hz, 1H); $^{13}$C NMR (100 MHz, CDCl$_3$) δ 171.35 (d, J$_{CP}$=4.0 Hz), 145.69 (d, J$_{CP}$=16.8 Hz), 135.34, 128.68, 128.59, 127.09, 121.54 (d, J$_{CP}$=148.8 Hz), 54.67 (d, J$_{CP}$=4.4 Hz), 52.06, 48.30 (d, J$_{CP}$=30.8 Hz), 36.81 (d, J$_{CP}$=4.6 Hz); $^{31}$P NMR (162 MHz, CDCl$_3$) δ 42.60; HRMS calculated for C$_{13}$H$_{16}$ClNO$_3$P (M+H)$^+$ required 300.0556, found 300.0583.

Characterization of the isolated diastereomer (17a$_2$) was as follows: R$_f$=0.17 (1:1 Hexanes/EtOAc); [a:]$^{25}$=-10.4; (c=0.08, CHCl$_3$); FTIR (neat) 1743, 1455, 1387, 1249 (P=O), 751, 700 cm$^1$; $^1$H NMR (400 MHz, CDCl$_3$) δ 7.32–7.22 (m, 5H), 7.10 (dddd, J$_{HP}$=51.6 Hz, J$_{HH}$=8.7, 1.9, 1.9 Hz, 1H), 6.32 (dddd, J$_{HP}$=35.7 Hz, J$_{HH}$=8.8, 2.1, 2.1 Hz, 1H), 4.53 (ddd, J$_{HH}$=8.0, 8.0 Hz, J$_{HH}$=8.0 Hz, 1H), 4.30 (dddd, J$_{HH}$=17.4, 12.9, 2.2 Hz, J$_{HP}$=2.2 Hz, 1H), 3.97 (dd, J=17.5, 2.0 Hz, 1H), 3.67 (s, 3H), 3.35 (dd J=13.8, 7.4 Hz, 1H), 3.09 (dd, J=13.8, 8.2 Hz, 1H); $^{13}$C NMR (100 MHz, CDCl$_3$) δ 171.00 (d, J$_{CP}$=4.4 Hz), 145.50 (d, J$_{CP}$=16.6 Hz), 136.11, 128.94, 128.66, 127.09, 121.92 (d, J$_{CP}$=148.9 Hz), 56.24 (d, J$_{CP}$=4.7 Hz), 52.31, 48.88 (d, J$_{CP}$=31.2 Hz), 36.55 (d, J$_{CP}$=2.3 Hz); $^{31}$P NMR (162 MHz, CDCl$_3$) δ 44.00; HRMS calculated for Cl$_3$H$_{16}$ClNO$_3$P (M+H)$^+$ required 300.0556, found 300.0569.

III. Preparation of Cyclic Phosphonamidate (17b)

A solution of compound (17a) (108 mg, 0.36 mmol) and CH$_2$Cl$_2$ (3 mL) was cooled in a 0° C. ice bath. Next, Et$_3$N (120 μL, 0.90 mmol) and DMAP (4.4 mg, 0.036 mmol) were added, followed by MeOH (36 mL, 0.90 mol). The reaction was warmed to room temperature and monitored by TLC. The reaction was concentrated under reduced pressure and subjected to flash chromatography (1:1 Hexanes/EtOAc) to afford 105 mg (99%/o) of (17b) as a separable mixture of two diastereomers (17b, and 17b$_2$) as colorless oils.

Characterization of the isolated diastereomer (17b$_1$) was as follows: R$_f$=0.56 (EtOAc); [α]$^{25}$=+118.5; (c=0.29, CHCl$_3$); FTIR (neat) 1740, 1455, 1385, 1347, 1228 (P=O), 751, 701 cm$^{-1}$; $^1$H NMR (400 MHz, CDCl$_3$) 67.28–7.18 (m, 5H), 7.02 (dddd, J$_{HP}$=43.0 Hz, J$_{HH}$=9.0, 2.0, 2.0 Hz, 1H), 6.00 (dddd, J$_{HP}$=29.8 Hz, J$_{HH}$=9.0, 2.1, 2.1 Hz, 1H), 4.36 (ddd, J$_{HH}$=8.8 Hz, J$_{HH}$=7.0, 7.0 Hz, 1H), 4.10–4.03 (m, 1H), 3.87 (dddd, J$_{HH}$=17.3, 6.2, 2.2 Hz, J$_{HH}$=2.2 Hz, 1H), 3.59 (s, 3H), 3.50 (d, J$_{HH}$=13.3 Hz, 3H), 3.27 (dd, J=13.7, 9.1 Hz, 1H), 3.05 (dd, J=13.7, 6.6 Hz, 1H); $^{13}$C NMR (100 MHz, CDCl$_3$) δ 171.95 (d, J$_{CP}$=3.2 Hz), 146.10 (d, J$_{CP}$=15.6 Hz), 136.12, 128.84, 128.42, 126.79, 117.49 (d, J$_{CP}$=159.2 Hz), 55.38 (d, J$_{CP}$=4.8 Hz), 52.89 (d, J$_{CP}$=6.5 Hz), 51.76, 48.12 (d, J$_{CP}$=29.0 Hz), 36.88 (d, J$_{CP}$=2.4 Hz); $^{31}$P NMR (162 MHz, CDCl$_3$) δ 41.20; HRMS calculated for C$_{14}$H$_{19}$NO$_3$P (M+H)$^+$ required 296.1052, found 296.1057.

Characterization of the isolated diastereomer (17b$_2$) was as follows: R$_f$=0.30 (EtOAc); [α]$^{25}$=-96.6; (c=0.47, CHCl$_3$); FTIR (neat) 1743, 1456, 1387, 1347, 1232 (P=O), 751, 702 cm$^{-1}$; $^1$H NMR (400 MHz, CDCl$_3$) δ 7.27–7.16 (m, 5H), 7.00 (dd, J$_{HP}$=43.0 Hz, J$_{HH}$=8.9 Hz, 1H), 5.94 (dddd, J$_{HP}$=29.6 Hz, J$_{HH}$=8.8, 2.0, 2.0 Hz, 1H), 4.31 (ddd, J$_{HP}$=10.1 Hz, J$_{HH}$=6.4, 6.4 Hz, 1H), 4.13 (dddd, J$_{HH}$=17.0, 4.1, 2.0 Hz, J$_{HP}$=2.0 Hz, 1H), 3.80 (dddd, J$_{HH}$=17.0, 5.3, 2.2 Hz, J$_{HP}$=2.2 Hz, 1H), 3.66 (s, 3H), 3.29 (dd, J=14.0, 5.4 Hz, 1H), 3.01 (dd, J=13.9, 10.2 Hz, 1H), 2.93 (d, J$_{HP}$=12.4 Hz, 3H); $^{13}$C NMR (100 MHz, CDCl$_3$) δ 171.84, 146.20 (d, J$_{CP}$=15.8 Hz), 137.08, 128.78, 128.56, 126.83, 117.64 (d, J$_{CP}$=158.0 Hz), 56.72 (d, J$_{CP}$=4.4 Hz), 52.14 (d, J$_{CP}$=6.5 Hz), 52.08, 48.55 (d, J$_{CP}$=28.5 Hz), 36.66 (d, J$_{CP}$=3.9 Hz); $^{31}$P NMR (162 MHz, CDCl$_3$) δ 41.91; HRMS calculated for C$_{14}$H$_{19}$NO$_3$P (M+H)$^+$ required 296.1052, found 296.1062.

Example 10

Scheme J depicts the reaction schemes followed in Parts I–II of this example.

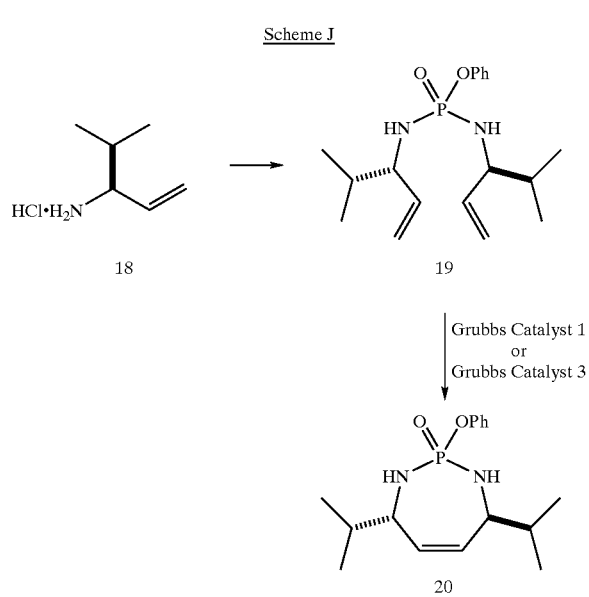

I. Preparation of Acyclic Valine-Derived, Phosphorus-Containing Compound (19)

A solution of phenyl dichlorophosphate (49 mg, 0.23 mmol) and CH$_2$Cl$_2$ (0.75 mL) was cooled in a 0° C. ice bath.

Next, Et$_3$N (186 mg, 1.84 mmol) and DMAP (3 mg, 25 μmol) were added slowly, and the solution was warmed to room temperature and stirred for 15 minutes. Valine-derived allylic ammonium salt (18) (68 mg, 0.50 mmol) was added, and the solution was stirred at room temperature for 2 hours, then brought to reflux for 90 minutes. The solvent was removed under reduced pressure, and the crude product was partitioned between EtOAc (10 mL) and water (10 mL). The layers were separated, and the aqueous layer was washed with EtOAc (3×2 mL). The organic layers were combined, dried (Na$_2$SO$_4$), and further concentrated under reduced pressure. Flash chromatography (2:1 Hexanes/EtOAc) afforded 76 mg (99%) of (19) as a white foam. [α]$^{25}$=+28.3 (c=0.12, CHCl$_3$); FTIR (neat) 1645, 1219 (P=O), 771, 690 cm$^{-1}$; $^1$H NMR (400 MHz, CDCl$_3$) δ 7.31–7.22 (m, 4H), 7.09 (t, J=7.3 Hz, 1H), 5.77 (ddd, J=16.9, 10.4, 6.4 Hz, 1H), 5.77 (ddd, J=16.9, 10.4, 6.4 Hz, 1H), 5.19 (d, J=17.1 Hz, 1H), 5.19 (d, J=17.1 Hz, 1H), 5.15–5.12 (m, 2H), 3.70–3.59 (m, 2H), 2.70 (dd, J$_{HH}$=10.2 Hz, J$_{HP}$=10.2 Hz, 1H), 2.66 (dd, J$_{HH}$=10.4 Hz, J$_{HH}$=10.4 Hz, 1H), 1.84–1.72 (m, 2H), 0.88 (d, J=6.9 Hz, 3H), 0.87 (d, J=6.6 Hz, 3H), 0.86 (d, J=7.0 Hz, 3H), 0.86 (d, J=6.5 Hz, 3H); $^{13}$C NMR (100 MHz, CDCl$_3$) δ 151.69 (d, J$_{CP}$=6.3 Hz), 138.65 (d, J$_{CP}$=3.4 Hz), 138.47 (d, J$_{CP}$=3.5 Hz), 129.40, 123.99, 120.28 (d, J$_{CP}$=5.1 Hz), 115.49, 115.45, 59.69, 59.38, 33.41 (d, J$_{CP}$=1.3 Hz), 33.35 (d, J$_{CP}$=2.1 Hz), 18.26, 18.12, 18.09, 18.02; $^{31}$P NMR (162 MHz, CDCl$_3$) δ 10.26; HRMS calculated for C$_{18}$H$_{30}$N$_2$O$_2$P (M+H)$^+$ required 337.2045, found 337.2052.

II. Valine-Derived P-Heterocycle (20)

A solution of compound (19) (143 mg, 0.43 mmol) and CH$_2$Cl$_2$ (14 mL) was purged with argon for 10 minutes. The solution was brought to reflux, and the Grubbs Catalyst 1 was added in three 5 mol % portions (17 mg, 21 μmol) over a 20-hour period. After 48 hours, the reaction was concentrated under reduced pressure and subjected to flash chromatography (2:1 Hexanes/EtOAc, then 1:2 Hexanes/EtOAc) to afford 47 mg (33%) of (19) and 61 mg (47%) of (20) as a white foam. An alternative approach using the Grubbs Catalyst 3 is as follows: A solution of compound (19) (6.2 mg, 18.4 μmol) and degassed CH$_2$Cl$_2$ (600 μL, CH$_2$Cl$_2$ was degassed by passing through a fritted filter under vacuum) was prepared. Grubbs Catalyst 3 (0.8 mg, 0.92 μmol) was added, and the solution was brought to reflux for 90 minutes and monitored by TLC. The reaction was concentrated under reduced pressure and subjected to flash chromatography (2:1 Hexanes/EtOAc, then 1:2 Hexanes/EtOAc) to afford 5.0 mg (88%) of (20) as a white foam. [α]$^{25}$=−22.5 (c=0.08, CHCl$_3$); FTIR (neat) 1593, 1224 (P=O), 769,691 cm$^{-1}$; $^1$H NMR (400 MHz, CDCl$_3$) δ 7.33–7.22 (m, 4H), 7.13 (t, J=7.5 Hz, 1H), 5.58–5.51 (m, 2H), 4.06 (ddd, J$_{HP}$=11.2 Hz, J$_{HH}$=7.2, 3.7 Hz, 1H), 3.87 (ddd, J$_{HP}$=11.4, J=7.6, 3.9 Hz, 1H), 3.00 (dd, J$_{HH}$=8.3, J$_{HP}$=8.3 Hz, 1H), 2.86 (dd, J$_{HH}$=6.2, J$_{HH}$=6.2 Hz, 1H), 1.94–1.86 (m, 1H), 1.86–1.77 (m, 1H), 1.01 (d, J=6.8 Hz, 3H), 0.96 (d, J=6.9 Hz, 3H), 0.89 (d, J=6.1 Hz, 3H), 0.87 (d, J=6.5 Hz, 3H); $^{13}$C NMR (100 MHz, CDCl$_3$) δ 150.94 (d, J$_{CP}$=6.4 Hz), 133.06, 132.31, 129.49, 124.41, 120.58 (d, J$_{CP}$=4.6 Hz), 54.86, 54.01 (d, J$_{CP}$=1.8 Hz), 33.41 (d, J$_{CP}$=12.3 Hz), 33.17 (d, J$_{CP}$=11.5 Hz), 18.78, 18.29, 17.55, 17.04; $^{31}$P NMR (162 MHz, CDCl$_3$) δ 16.42; HRMS calculated for C$_{16}$H$_{26}$N$_2$O$_2$P (M+H)$^+$ required 309.1732, found 309.1731.

Example 11

The inhibition of Herpes Simplex Virus Protease by three different compounds was determined according to the procedure described by Waxman et al., *Antiviral Chemistry and Chemotherapy*, 11:1–22 (1999); Qiu et al., *Proteases of Infectious Agents*, Academic Press, 93–115 (1999); and U.S. Pat. No. 6,008,033, each incorporated by reference herein.

The compounds tested are shown in Schemes K, L, M, N, and O with the concentrations of each of the compounds being 200 μmolar.

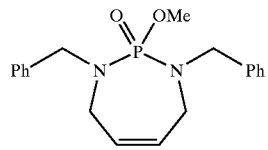

Scheme K

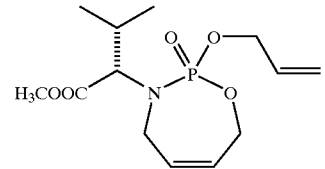

Scheme L

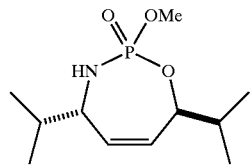

Scheme M

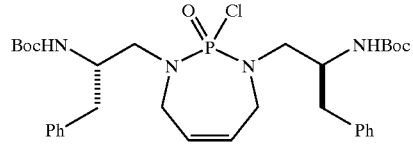

Scheme N

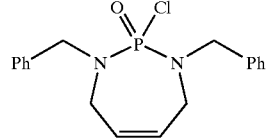

Scheme O

The Scheme K compound resulted in a 25.5% inhibition of the protease. The Scheme L compound resulted in a 34.7% inhibition of the protease. Finally, the Scheme M compound resulted in a 33.5% inhibition of the protease, the Scheme N compound resulted in a 44.4% inhibition of the protease, and the Scheme O compound resulted in a 44.7% inhibition of the protease.

Example 12

The inhibition of HIV protease by the compounds shown in Scheme N (99 μmolar) and Scheme O (99 μmolar) was determined following the procedure described by Maschera et al., Human Immunodeficiency Virus: Mutations in the Viral Protease that Confer Resistance to Saquinavir Increase the Dissociation Rate Constant for the Protease-Saquinavir Complex, *J. Biol. Chem.*, 271:33231–35 (1996), incorporated by reference herein.

The compound of Scheme N resulted in a 23% inhibition of the protease, while the compound of Scheme O resulted in a 36% inhibition.

Example 13

The inhibition of human cathepsin K by the compound shown in Scheme N (106 μmolar) was determined. The peptides utilized were chromophoric Z-Phe-Arg-pNA*HCl and fluorogenic Z-Phe-Arg-AMC (each available from BACHEM Bioscience, Inc.). Stock solutions were prepared with 100% dimethylsulfoxide (DMSO) and stored at −20° C.

The final assay conditions were 100 mM NaOAc, pH of 5.5, 10 mM (R,R)-dithiothreitol (DTT), 10% DMSO, 120 mM NaCl, 10 μmolar of the peptide, and 12.5–0.012 μmolar inhibitor in twofold serial dilutions from 20× stocks in 100% DMSO. The enzyme working solution was a 1:3000 dilution of 8.75 mM human cathepsin K into 100 mM of NaOAc, pH of 5.5, 10 mM DTT, 1.2 M NaCl.

Serial dilutions were performed in 100% DMSO. Columns 2–12 of an intermediate plate were filled with 100 mL/well of 100% DMSO and column 1 was filled with 195 mL/well. Next, 5 mL of a 10 mM solution was added to column 1. A twofold serial dilution was prepared in columns 1–11 of the intermediate plate by sequential transfer of 100 mL of the contents of each well in a column to the corresponding well of the next column, with mixing between each transfer. Samples of 11.7 mL from each well of the intermediate plate were transferred to another intermediate plate and 200 mL of a peptide buffer (105 mM NaOAc, pH of 5.5, 10.5 mM DTT, 5.8% DMSO, 12 mM peptide) was added. Samples (20 μL) of enzyme working solution were placed in each well of an empty assay plate, and 180 μL/well of the test compound-peptide mixture was added to the enzyme to initial the assay. The fluorescence was monitored every 6 minutes for 72 minutes using a CytoFluor Series 4000 PerSeptive Biosystems multi-well fluorescence plate reader with the following settings: gain=50; 20 reads/well; 32° C.; lex=360±20 nm; and lem=440±120 nm.

The compound resulted in a 34% inhibition of human cathepsin K.

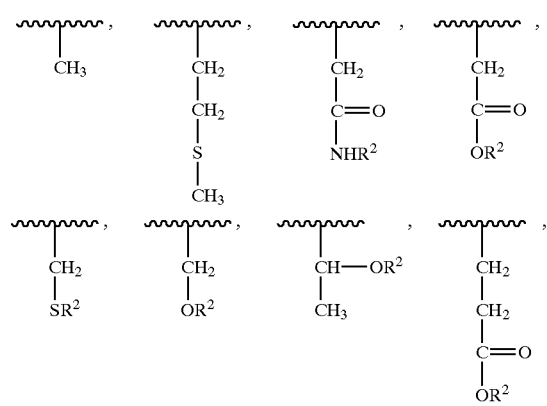

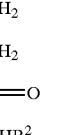
wherein each R² is individually selected from the group consisting of hydrogen, branched and unbranched alkyl groups, branched and unbranched alkenyl groups, branched and unbranched alkynyl groups, allyl groups, acyl groups, aryl groups, and benzyl groups.
3. The compound of claim 1, wherein said formula is selected from the group consisting of
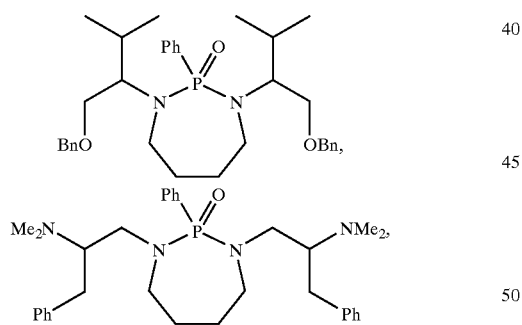

We claim:

1. A compound according to a formula selected from the group consisting of

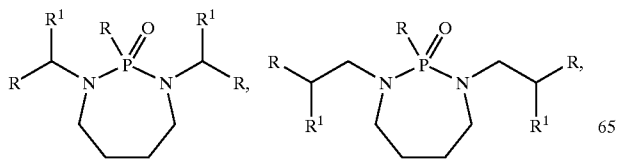

-continued

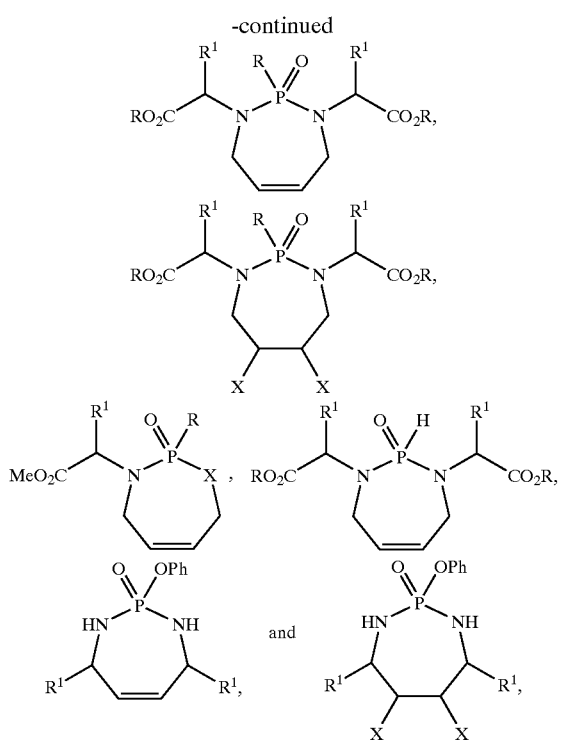

wherein:

each X is individually selected from the group consisting of oxygen, —NH, and —NOR;

each R is individually selected from. the group consisting of hydrogen, branched and unbranched alkyl groups, branched and unbranched alkenyl groups, branched and unbranched alkynyl groups, allyl groups, aryl groups, acyl groups, 2–15 mer peptides, and benzyl groups; and each $R^1$ is individually selected from the group consisting of hydrogen, amino acid side chains, and 2–15 mer peptides.

2. The compound of claim 1, wherein at least one $R^1$ comprises an amino acid side chain selected from the group consisting of